(12) United States Patent
Davies et al.

(10) Patent No.: US 7,883,032 B2
(45) Date of Patent: Feb. 8, 2011

(54) DEVICES AND FORMULATIONS

(75) Inventors: Lee Adrian Davies, Wolverhampton (GB); David Neville Davies, Oxford (GB); Margaret Sin Ka Wan, Oxford (GB); Ronald Alan Coffee, Surrey (GB)

(73) Assignee: Battelle Memorial Institute, Columbus, OH (US)

( * ) Notice: Subject to any disclaimer, the term of this patent is extended or adjusted under 35 U.S.C. 154(b) by 1073 days.

(21) Appl. No.: 10/240,356

(22) PCT Filed: Apr. 3, 2001

(86) PCT No.: PCT/GB01/01529

§ 371 (c)(1),
(2), (4) Date: May 16, 2003

(87) PCT Pub. No.: WO01/74431

PCT Pub. Date: Oct. 11, 2001

(65) Prior Publication Data

US 2003/0173219 A1    Sep. 18, 2003

(30) Foreign Application Priority Data

Apr. 3, 2000  (GB) ................................ 0008116.6
Jun. 29, 2000  (GB) ................................ 0016031.7

(51) Int. Cl.
*B05B 5/00*    (2006.01)
(52) U.S. Cl. ..................... 239/690; 239/690.1; 239/692
(58) Field of Classification Search ..................... 239/3, 239/690, 690.1–692; 128/200.26, 202.25, 128/200.25, 202.26
See application file for complete search history.

(56) References Cited

U.S. PATENT DOCUMENTS

| 1,599,111 | A | 9/1926 | Beadle |
| 4,439,421 | A | 3/1984 | Hooper et al. |
| 4,659,012 | A | 4/1987 | Coffee |
| 4,829,996 | A | 5/1989 | Noakes |
| 4,851,211 | A | 7/1989 | Adjei et al. |

(Continued)

FOREIGN PATENT DOCUMENTS

EP    0234842 A    9/1987

(Continued)

OTHER PUBLICATIONS

Electrosols Limited International Search Report for PCT/GB01/01529 filed Apr. 3, 2001.

(Continued)

*Primary Examiner* — Len Tran
*Assistant Examiner* — Jason J Boeckmann
(74) *Attorney, Agent, or Firm* — Frost Brown Todd LLC

(57) ABSTRACT

Methods are described of delivering biological material, which methods include the steps of providing a liquid formulation containing the biological material, supplying the liquid formulation to an outlet and subjecting liquid issuing from the outlet to an electrical field thereby causing electrohydrodynamic processing of the liquid without denaturing the biological material. In one example, the liquid formulation is provided by removing salts from a formulation containing biological material that does not denature in alcohol and then adding an alcohol to the formulation before supplying the liquid formulation to the outlet. An acid may be added to the liquid formulation before supplying the liquid formulation to the outlet.

13 Claims, 14 Drawing Sheets

U.S. PATENT DOCUMENTS

| | | | |
|---|---|---|---|
| 4,962,885 A | | 10/1990 | Coffee |
| 5,115,971 A | | 5/1992 | Greenspan et al. |
| 5,192,528 A | | 3/1993 | Radhakrishnan et al. |
| 5,279,940 A | * | 1/1994 | Kissel ............................ 435/6 |
| 5,578,567 A | | 11/1996 | Cardinaux |
| 5,660,166 A | | 8/1997 | Lloyd |
| 5,743,250 A | | 4/1998 | Gonda et al. |
| 5,813,614 A | | 9/1998 | Coffee |
| 5,873,523 A | | 2/1999 | De La Mora |
| 5,915,377 A | | 6/1999 | Coffee |
| 5,945,111 A | | 8/1999 | Esser |
| 5,992,771 A | * | 11/1999 | Noakes et al. ............. 239/690.1 |
| 6,068,199 A | * | 5/2000 | Coffee ............................ 239/3 |
| 6,103,271 A | * | 8/2000 | Morrison et al. ............. 424/490 |
| 6,105,571 A | | 8/2000 | Coffee |
| 6,105,877 A | | 8/2000 | Coffee |
| 6,123,068 A | | 9/2000 | Lloyd |
| 6,158,431 A | | 12/2000 | Poole |
| 6,252,129 B1 | * | 6/2001 | Coffee ............................ 602/42 |
| 6,302,331 B1 | | 10/2001 | Dvorsky |
| 6,318,640 B1 | | 11/2001 | Coffee |
| 6,386,195 B1 | * | 5/2002 | Coffee ................... 128/200.14 |
| 6,471,943 B1 | * | 10/2002 | Placke et al. .................. 424/45 |
| 6,485,706 B1 | | 11/2002 | McCoy et al. |
| 6,503,481 B1 | * | 1/2003 | Thurston et al. .............. 424/45 |
| 6,595,208 B1 | * | 7/2003 | Coffee et al. ........... 128/203.12 |
| 6,684,879 B1 | * | 2/2004 | Coffee et al. ........... 128/200.14 |
| 6,849,263 B2 | | 2/2005 | Modi |
| 7,087,215 B2 | | 8/2006 | Modi |
| 7,112,561 B2 | | 9/2006 | Gyurik et al. |
| 7,193,124 B2 | | 3/2007 | Coffee |
| 7,244,703 B2 | | 7/2007 | Gyurik et al. |
| 7,255,102 B2 | | 8/2007 | Modi |
| 7,303,762 B2 | | 12/2007 | New |
| 2001/0003148 A1 | * | 6/2001 | Coffee ............................ 602/42 |
| 2003/0173219 A1 | | 9/2003 | Davies et al. |
| 2004/0079360 A1 | * | 4/2004 | Coffee et al. ........... 128/200.14 |

FOREIGN PATENT DOCUMENTS

| | | |
|---|---|---|
| EP | 0 501 725 | 9/1992 |
| EP | 0919242 A | 6/1999 |
| FR | 1 146 256 | 11/1957 |
| GB | 1 569 707 | 6/1980 |
| GB | 2 273 673 | 6/1994 |
| GB | 2273893 A | 7/1994 |
| HU | 62473 | 5/1993 |
| WO | WO 8907603 A | 8/1989 |
| WO | WO 9412285 A | 6/1994 |
| WO | WO9414543 | 7/1994 |
| WO | WO 95/26235 | 10/1995 |
| WO | WO 96/40441 | 12/1996 |
| WO | WO 97-46243 | 12/1997 |
| WO | WO 9803267 | 1/1998 |
| WO | WO 98/29097 | 7/1998 |
| WO | WO 99/01463 | 1/1999 |
| WO | WO 99/07478 | 2/1999 |
| WO | WO 99/33853 | 7/1999 |
| WO | WO 99/42153 | 8/1999 |
| WO | WO 99/44664 | 9/1999 |
| WO | WO 99/49981 | 10/1999 |
| WO | WO 9949923 A | 10/1999 |
| WO | WO 0035524 A | 6/2000 |
| WO | WO 00/38770 | 7/2000 |
| WO | WO 00/47203 | 8/2000 |
| WO | WO 0066206 | 11/2000 |
| WO | WO 01/74431 | 10/2001 |

OTHER PUBLICATIONS

Brown, A., "Propellant-Driven Aerosols of Proteins," Aerosol Science and Technology, vol. 24 (1996) pp. 45-56.

Chamberlain, M.J. et al., "Factors influencing the deposition of inhaled particles in man," Clinical Science, vol. 64 (1983) p. 69-78.

Chawla, A. et al., "Aggregation of Insulin, Containing Surfactants, in Contact with Different Materials," Diabetes, vol. 34 (May 1985) pp. 420-424.

Choi, W.S. et al., "Inhalation delivery of proteins from ethanol suspensions," PNAS, vol. 98(20) (Sep. 25, 2001) pp. 11103-11107.

Gonda, I., "Aerosols for delivery of therapeutic and diagnostic agents to the respiratory tract," Critical Reviews in Therapeutic Drug Carrier Systems, vol. 6 (1990) pp. 273-313.

International Search Report dated Feb. 4, 2002 for PCT/GB01/01529.

International Search Report dated Jun. 15, 1999 for PCT/IB99/00469.

Sluzky, V. et al., "Mechanism of Insulin Aggregation and Stabilization in Agitated Aqueous Solutions," Biotechnology and Bioengineering, vol. 40 (1992) pp. 895-903.

* cited by examiner

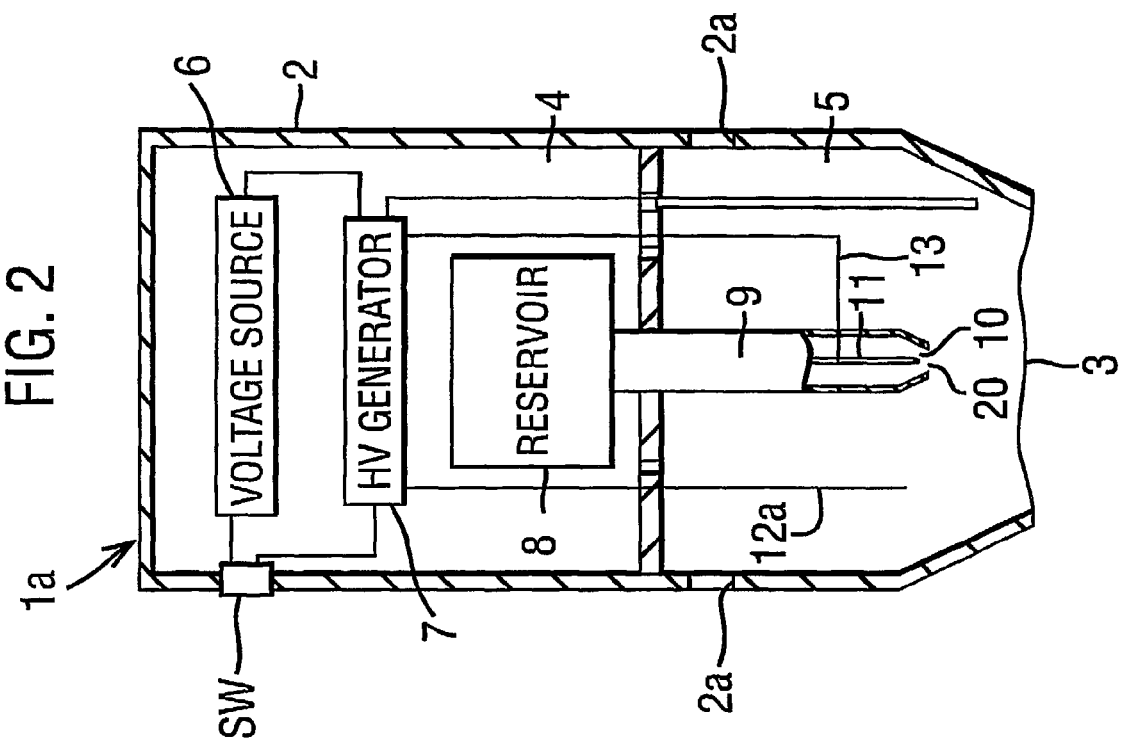
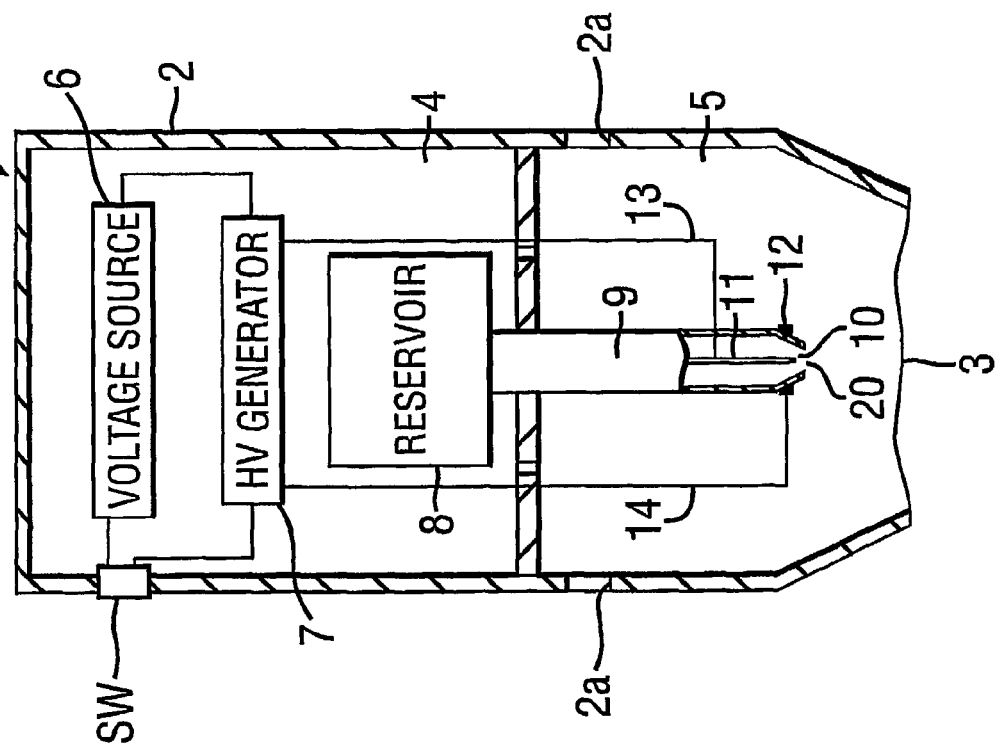

FIG. 6

Kb   pCIKβGaL   Jet   Ultra   EHD   Kb

FIG. 7
EHD aerosols can be used even with larger plasmids

Kb   pCIKCAT   pCIKCFTR.10   pREP8βGal   Kb

*Plasmids as large as 14.2Kb show no degradation following aerosolization

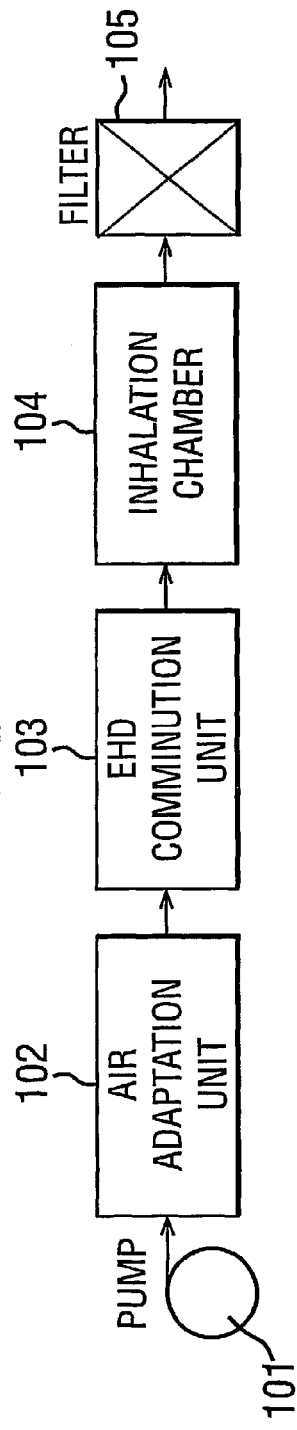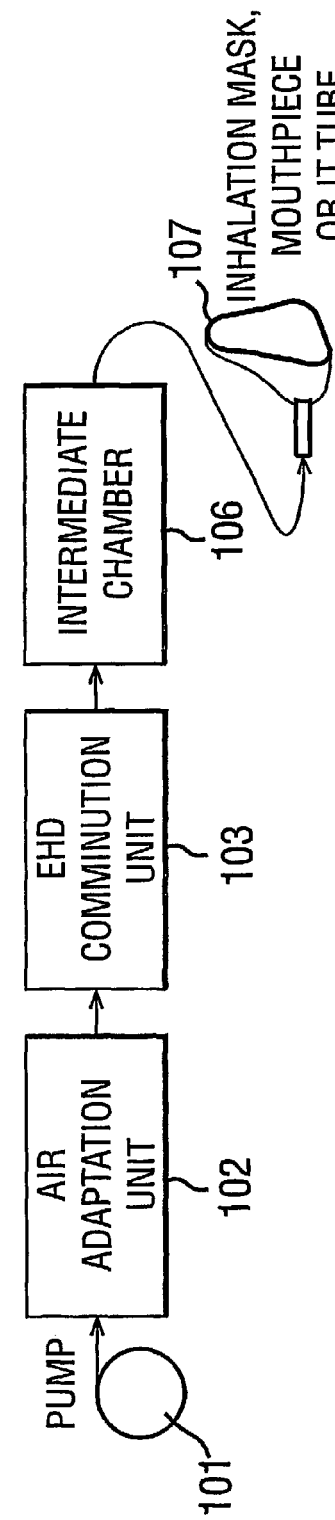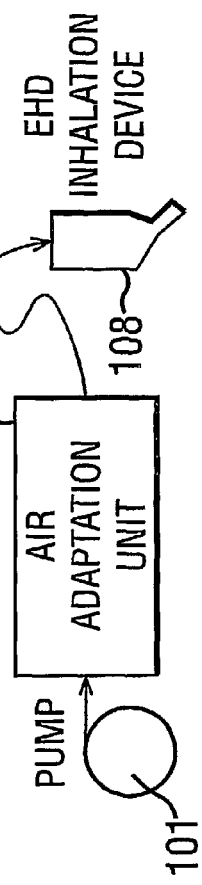

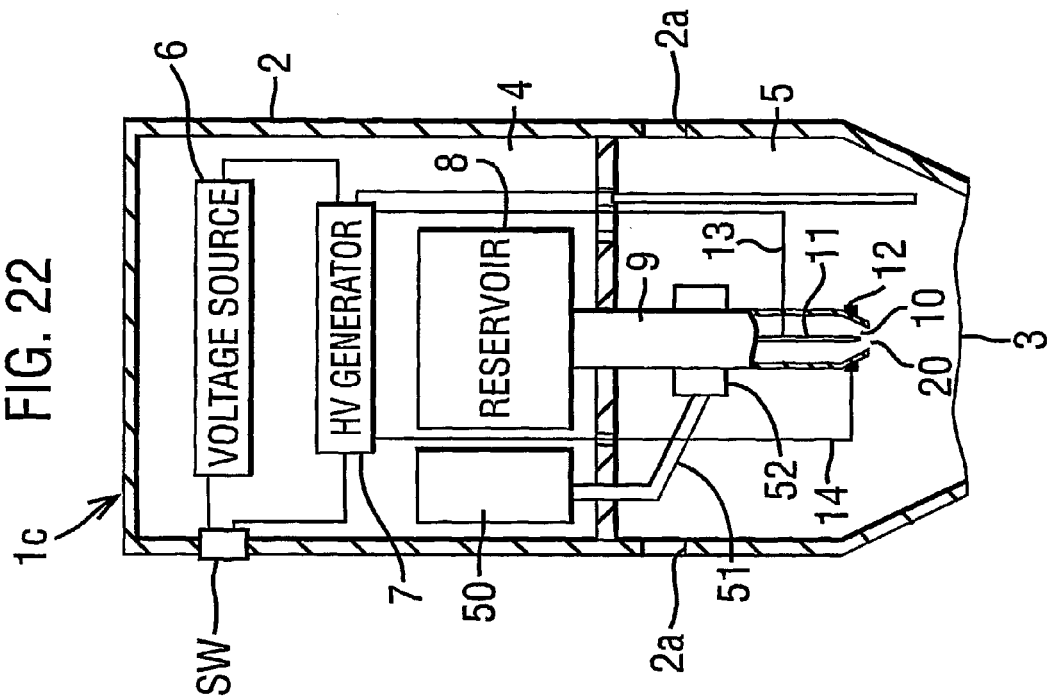
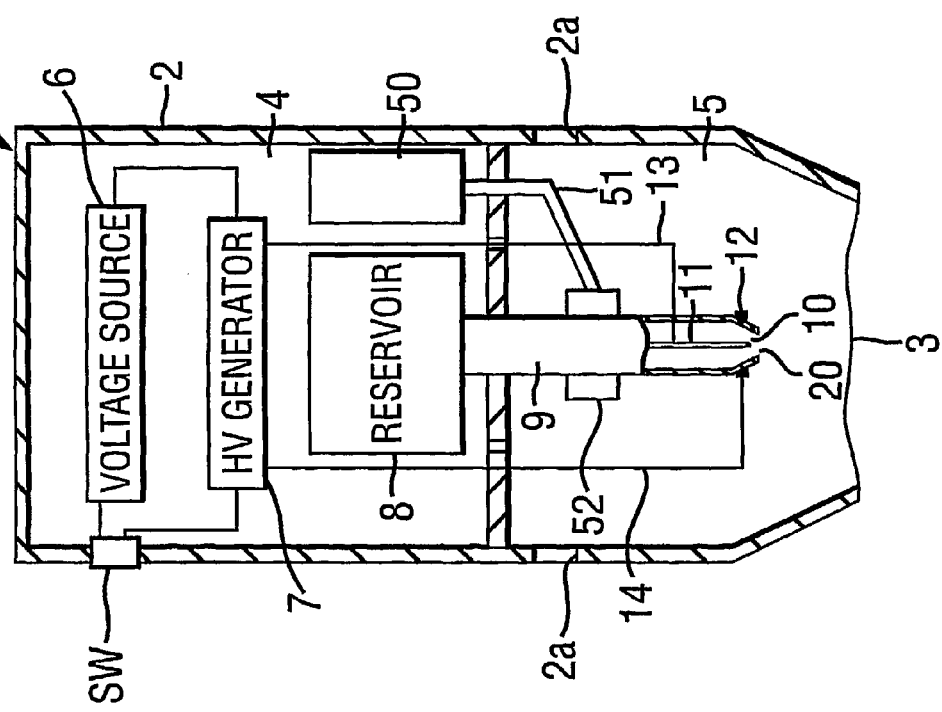

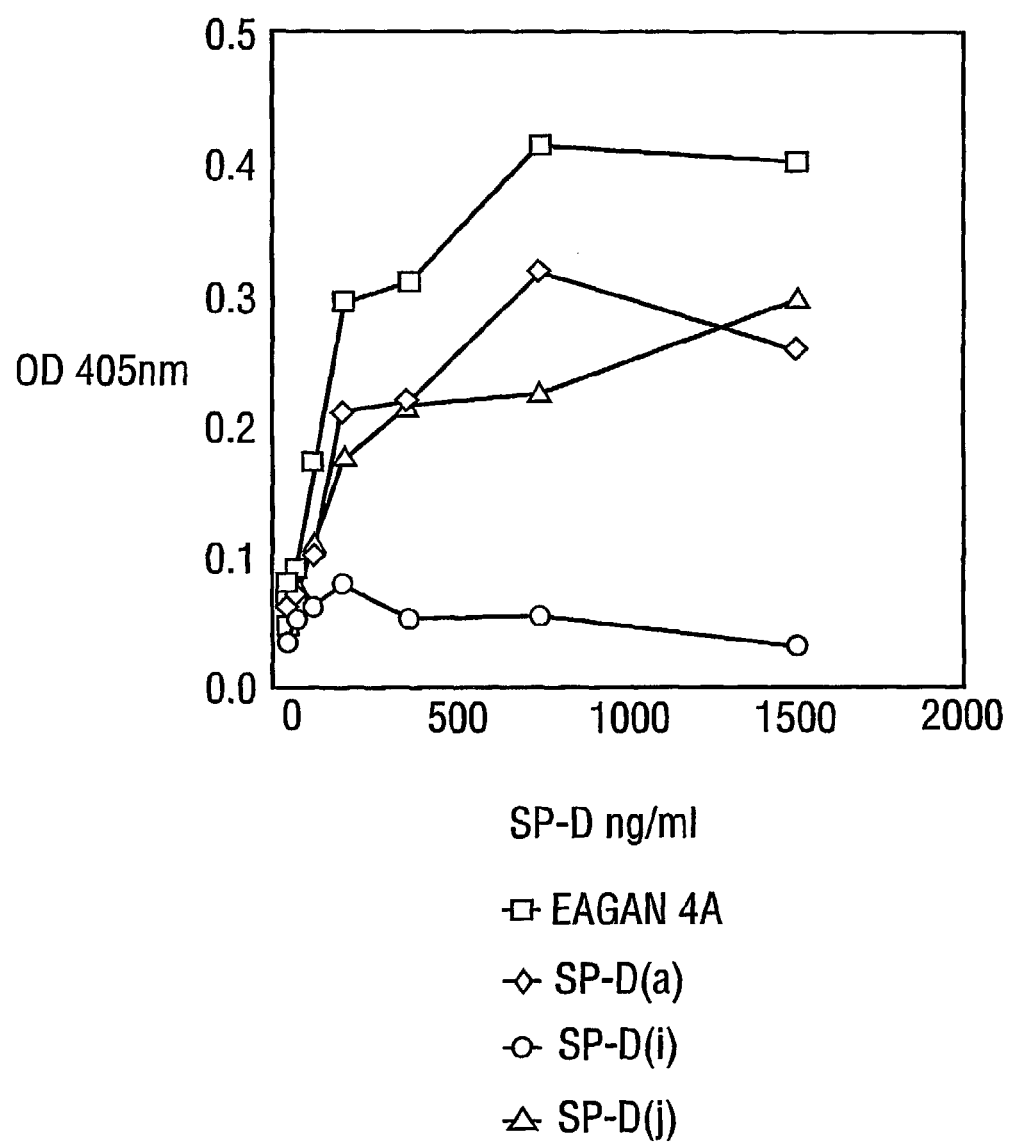

DEVICES AND FORMULATIONS

TECHNICAL FIELD

This invention relates to methods and devices for processing liquids using electric fields, in particular but not exclusively to methods and devices for comminuting relatively highly conductive liquid formulations such as aqueous formulations using electric fields.

BACKGROUND OF THE INVENTION

A method of processing liquids using electric fields is described in, for example, GB-A-1569707. In this method, which is known as the electrohydrodynamic method (sometimes also referred to herein as "EHD"), liquid issuing from an outlet is subjected to an electric field such that the net electrical charge in the liquid as the liquid emerges into free space or air counteracts the surface tension forces of the liquid and the repulsive forces generated by the like electrical charges result in a cone and jet. Depending upon the liquid formulation, the liquid jet may then, as described in GB-A-1569707, breakup into liquid droplets, or may, as described in, for example, the applicant's WO 98/03267 (the whole contents of which are incorporated by reference), break up to form solid or gel-like particles or may form a continuous fibre which may break-up into short lengths ("fibrils"). The products resulting from the electrodynamic method are, for convenience, collectively referred to herein as "electrosols".

This electrohydrodynamic method is particularly good at controlling the dimensions of the resultant product and provides an extremely efficient way of delivering drugs or medicaments to the respiratory system, for example to the pulmonary system, and to other epithelial or topical surfaces such as wound surfaces as described in WO 98/03267. Furthermore, as described in WO 98/03267 electrohydrodynamic methods may be used to spray complex colloids, provided the colloid is initially in a substantially liquid form.

The electrohydrodynamic method enables sprays or clouds of droplets ("aerosols") to be produced in which the droplets are monodispersed, that is they have a very uniform size and does not, unlike some conventional aerosol producing methods, require a propellant gas. This makes inhalers using the electrohydrodynamic method such as described in the applicant's U.S. Pat. No. 4,962,885, U.S. Pat. No. 6,105,877, U.S. Pat. No. 6,105,571, U.S. Pat. No. 5,813,614, U.S. Pat. No. 5,915,377 and WO 99/07478 (which enable delivery of at least partially electrically discharged droplets) and WO 00/35524 (which enables delivery of electrically charged droplets) particularly advantageous because the absence of a gas propellant makes the inhaler easy to use as inhalation does not have to be timed with the expulsion of gas from the inhaler and the monodispersed nature of the aerosol combined with the ability provided by the electrohydrodynamic method to control the size of the droplets enables drugs or other medicaments to be targeted to a particular region of the respiratory system, for example a specific region of the lung. The whole contents of U.S. Pat. No. 4,962,885, U.S. Pat. No. 6,105,877, U.S. Pat. No. 6,105,571, U.S. Pat. No. 5,813,614, U.S. Pat. No. 5,915,377, WO 99/07478, and WO 00/35524 are hereby incorporated by reference.

As more is understood about the way biological species operate, veterinary and medical treatments increasingly incorporate biological molecules or material such as DNA, RNA, proteins, peptides, hormones, lipids, cytokines, etc. into therapies, treatments and prophylactic medicaments such as vaccines. As used herein the term "biological material" includes biological molecules, biological molecule fragments such as DNA fragments and recombinant biomolecules, including proteins such as enzymes and other biological material of a similar size. These biological materials vary in their complexity but some, particularly proteins and DNA, are extremely sensitive to their immediate surroundings and can easily be broken down or denatured which can reduce their activity and even eliminate it altogether. The delivery of biological material also requires the occasional use of isotonic or buffered liquid vehicles, and because such materials are often expensive to produce, delivery systems must be as efficient as possible.

Traditional methods of atomising liquids of this kind, such as air-jet or ultrasonic nebulization, impart large shear forces on the carrier liquid and hence also on the biological material inside. Shear forces of this magnitude are known to denature sensitive biological materials such as DNA or proteins and thus there is no readily available delivery method that is immediately suitable for therapies that use such biological materials.

The carrier liquids for the biological material mentioned above are generally aqueous and relatively highly conductive. Unfortunately, EHD is well known to have difficulty in spraying conductive liquids. Numerous patents and published papers indicate that the resistivity of the liquid to be sprayed must be above 10,000 Ohm.m. Liquids below this will spray, but there seems to be a cut-off at around 100 Ohm.m, below which no aqueous-based formulation will spray in air. This is partly due to the surface tension of water which is high, approximately 72 mN/m (milli Newtons per metre), and partly due to the polar nature of water, which makes any impurities such as a water soluble drug contribute significantly to the liquid conductivity. This has meant that non-aqueous solvents such as ethanol tend to be used for EHD.

Furthermore, EHD comminution uses high voltages (1 KV and above) to break up liquid formulations by direct counteraction of the surface tension of the liquid. The use of such high voltages raises several potential practical problems, namely: 1) that the electric field might directly influence, denature or break up delicate, for example biological, materials in the liquid; 2) that breaking up the bulk liquid into small droplets might physically denature such delicate biological materials through excessive shear forces; and 3) that air which breaks down around the nozzle might create ozone which will react with any water in the formulation to produce hydrogen peroxide which is itself a strong oxidant and the presence of which could lead to molecular denaturation.

These problems have meant that EHD has to date only really been practical for small, robust molecules, such as salbutamol and budesonide, which have good solubility in alternative solvents like ethanol. However, ethanol is not a good solvent for biological materials because it can cause precipitation (as it does for DNA) and denaturation (as it does for delicate proteins).

SUMMARY OF THE INVENTION

In one aspect, the present invention provides a method of enabling EHD to be used with highly conductive, generally aqueous, liquids.

In one aspect, the present invention provides a method of enabling EHD to be used to dispense biological materials such as DNA, RNA, proteins, peptides, hormones, lipids, cytokines and recombinant biomolecules.

In one aspect, the present invention provides a method of controlling processing of liquid using EHD wherein the partial vapour pressure of a volatile component of a liquid is controlled in the region adjacent to where the liquid is subject to the electric field.

In one aspect, the present invention provides a method of controlling electrohydrodynamic comminution of an aqueous liquid formulation to produce droplets, wherein the air in the region into which the liquid issues is dried or dehumidified to cause evaporation to reduce the size of the droplets. This should facilitate production of droplets for supply to the respiratory system of babies and even very small mammals, such as mice.

In one aspect, the present invention provides an EHD inhalation apparatus capable of delivering biological material and other delicate molecules or compounds such as drugs to humans and animals such as mice, In one aspect, the present invention provides devices and methods which enable generation of respirable droplets containing delicate, aqueous-based molecules that is superior to any other method currently available.

In one aspect the present invention provides an electrohydrodynamic comminution device which causes no denaturation of biological material or sensitive molecules, and thus benefits from producing comminutes with controlled diameter and charge.

In one aspect the present invention provides a method for spraying delicate molecules or biological material without denaturation.

In one aspect the present invention provides a method of modifying the product of EHD processing by air preparation that enables product consistency (that is whether the product is solid, gel or liquid) and droplet size to be changed by affecting local evaporation characteristics for the liquid.

In one aspect the present invention provides a formulation for preparing DNA in solution which adds ethanol without precipitating out the DNA.

In one aspect the present invention provides a method of spraying DNA by EHD wherein an acid (e.g. acetic acid) is added in order to make DNA containing solutions sprayable at higher concentrations.

In one aspect the present invention provides a method of spraying DNA by EHD wherein EDTA or Catalase is added to the liquid to be sprayed to prevent DNA degradation.

In one aspect the present invention provides a method of spraying DNA by EHD wherein aqueous or high surface tension formulations are made sprayable by adding increased quantities of surfactants, generally at a concentration significantly above the Critical Micelle Concentration.

In one aspect the present invention provides a method that enables aqueous or highly conductive formulations to be sprayed by EHD by the addition of at least one long chain polymer (e.g. PVP, PVA, ethyl cellulose) to the liquid to be sprayed.

In one aspect the present invention provides a method of enabling spraying by EHD of formulations which normally form unstable sprays by adding polymer (either a single polymer or a combination of polymers) to the liquid to be sprayed.

In one aspect the present invention provides a method of enhancing sprayability of a formulation by EHD by adding surfactant and polymer to the liquid formulation to be sprayed.

In one aspect the present invention provides a method of spraying biological material by EHD wherein polymer is added to the biological material-containing liquid formulation to be sprayed. This protects and stabilises the delicate biological material within the liquid formulation.

In one aspect the present invention provides a method of making formulations sprayable by EHD at either polarity by the addition of polymers to the formulation.

This enables use of the twin nozzle or outlets devices described in U.S. Pat. No. 6,105,877 and U.S. Pat. No. 5,915,377 to spray aqueous formulations.

In an embodiment, devices and methods are provided that enable electrohydrodynamic comminution of aqueous liquids containing drums and/or biological material to produce sprays or dispensions which are ideal for respiration and delivery to the internal epithelia, including the lung, trachea, throat, mouth and nasal passages, and could also be advantageous for all topical applications.

BRIEF DESCRIPTION OF THE DRAWINGS

Embodiments of the present invention will now be described, by way of example, with reference to the accompanying drawings, in which:

FIG. 1 shows a schematic part-cross-sectional view of a first example of a dispensing device;

FIG. 2 shows a schematic part-cross-sectional view of a second example of a dispensing device;

FIG. 6 shows a photograph of an electrophoretic gel plot of DNA traces for comparing the amount of degradation obtained when a method embodying the present invention is used to produce a nebulized or atomised droplet spray containing the DNA with the amount of degradation obtained when other methods are used to produce a nebulized or atomised droplet spray containing DNA;

FIG. 7 shows a photograph of an electrophoretic gel plot of DNA traces, illustrating the lack of degradation for various DNA plasmids when a method embodying the present invention is used to produce a nebulized or atomised droplet spray containing the DNA plasmid;

FIGS. 12 to 14 show block diagrams of different inhalation apparatus for delivering electrosol for inhalation;

FIG. 21 shows a schematic part-cross-sectional view of a modified version of the dispensing device shown in FIG. 1;

FIG. 22 shows a schematic part-cross-sectional view of a modified version of the dispensing device shown in FIG. 2; and FIG. 23 shows a graph illustrating the binding of rSP-D to Eagan 4A LPS after incubation with various solvents.

DETAILED DESCRIPTION OF THE INVENTION

Figure 3:
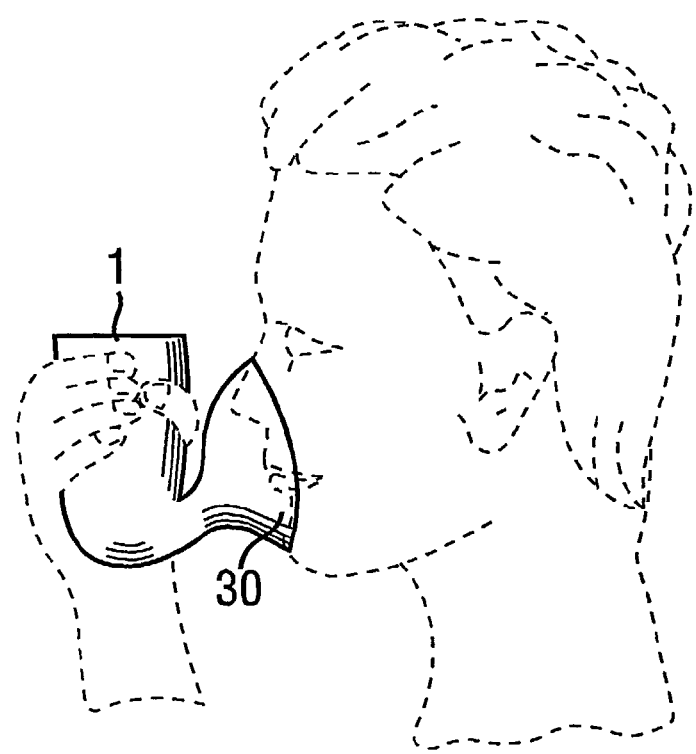
FIGS. 3 and 4 show examples of use of a dispensing device as an oral and nasal inhaler, respectively.

Referring now to FIG. 1, there is shown a dispensing device 1 suitable for use in methods embodying the invention to be described in detail below. The device 1 has a housing 2 which is generally formed of an electrically insulative material. The housing 2 has an outlet 3 and is divided into first and second chambers 4 and 5. The second chamber 5 has air inlets 2a. The first chamber contains a voltage source 6 such as a battery, a high voltage generator 7 for generating a high voltage (of the order of kilovolts) from the battery voltage and a reservoir 8 for containing the liquid to be subjected to electrohydrodynamic processing. The reservoir is coupled to a, in this example, generally insulative liquid supply tube 9 which extends into the second chamber 5 and has an outlet 10 in the second chamber 5. Liquid may be supplied from the reservoir 8 to the liquid supply tube 9 under gravity or by means of a pump as described in any of U.S. Pat. No. 4,962,885, U.S. Pat. No. 6,105,877, U.S. Pat. No. 6,105,571, U.S. Pat. No. 5,813,614, U.S. Pat. No. 5,915,377, WO 99/07478 and WO 00/35524. A user operable switch SW is provided to enable a user to couple the voltage source 6 to the high voltage generator 7.

In this example a comminution site is provided by establishing a high voltage between a first conductive electrode 11 supported within the tube 9 and a second electrode 12 provided on the outer surface of the tube 9. The first and second electrodes are coupled to a high voltage and an earth (ground) supply lead 13 and 14, respectively, of the high voltage generator 7.

When a user operates the switch SW to couple the voltage source 6 to the high voltage generator 7 a high voltage (generally of the order of kilo volts) is provided between the first and second electrodes causing an electric field to be established in a comminution region 20 adjacent the outlet 10. Liquid issuing from the outlet is thus subjected to this electric field such that the net electrical charge in the liquid as the liquid emerges into free space or air counteracts the surface tension forces of the liquid and the repulsive forces generated by the like electrical charges result in a cone and jet which, depending upon the liquid formulation, may then break up into liquid droplets.

The dispensing device 1 produces an electrically charged comminution. Further details and modifications of this device can be found in WO00/35524.

Any of the comminution site arrangements described in any of U.S. Pat. No. 4,962,885, U.S. Pat. No. 6,105,877, U.S. Pat. No. 6,105,571, U.S. Pat. No. 5,813,614, U.S. Pat. No. 5,915,377, WO99/07478 and WO 00/35524 may be used in place of the comminution site described above. Also, the device shown in FIG. 1 may be modified to enable at least partial discharge of the electrically charged comminution in any of the ways described in U.S. Pat. No. 4,962,885, U.S. Pat. No. 6,105,571, U.S. Pat. No. 5,813,614, and GB-A-1569707.

FIG. 2 shows a dispensing device 1a based on that described in WO99/07478 in which the second electrode 12 is replaced by a discharge electrode 12a spaced from the tube 9 and in which a further or deflection electrode 13 is provided. In this case the high voltage generator 7 is arranged to maintain the further electrode 13 at a voltage intermediate the voltages applied to the first and discharge electrodes 11 and 12a. The further electrode 13 serves, as described WO99/07478, to deflect the comminution away from the discharge electrode 12a until sufficient space charge has been generated by production of a comminution. The device 1a may be modified to have the same construction as any of the embodiments described in WO 99/07478 or any of the modifications of the embodiments described in WO 99/07478.

Figure 4:
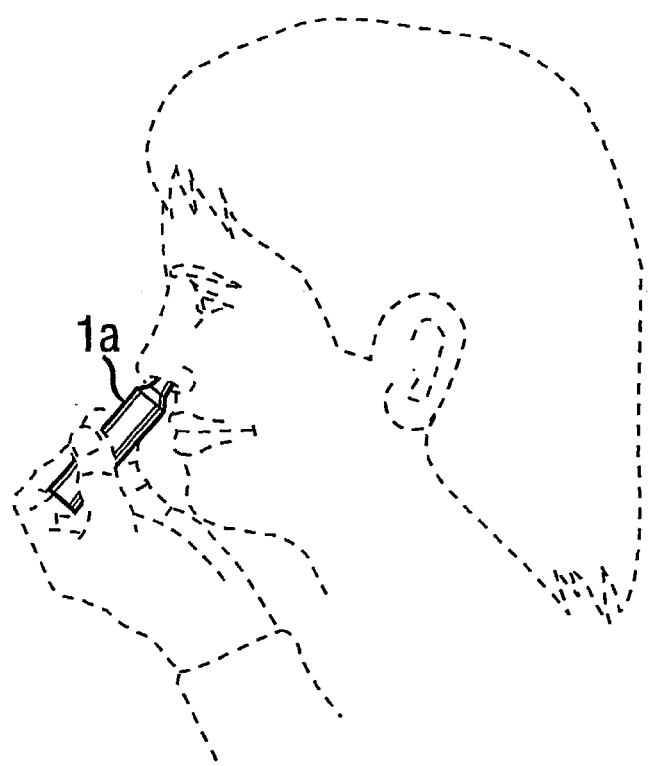

The dispensing devices 1 and 1a shown in FIGS. 1 and 2 may be used to dispense comminuted matter into a chamber or, especially where the comminuted matter is electrically charged, onto a surface. In these cases the second electrode 12 shown in FIG. 1 may be omitted and an earth may be provided at or by the surface to which the spray is directed. Also, the outlet 3 may as illustrated diagrammatically in FIG. 3 be coupled to a mouthpiece 30 to enable oral inhalation of the comminuted matter by a human user or may be adapted to be received against or slightly within a nostril of a human user as shown in FIG. 4 to enable nasal inhalation.

Methods embodying the invention of enabling electrohydrodynamic processing (otherwise referred to herein as spraying) of liquids will now be described.

Method 1

A method will now be described of enabling electrohydrodynamic comminution of an aqueous solution containing biological material such as DNA. EHD formulations often incorporate ethanol because it has a low conductivity and a low surface tension. It can be added to most formulations, but with DNA its addition conventionally causes precipitation. In fact, the addition of ethanol is actually taught as a means of precipitating DNA out of solution (see for example "Molecular Cloning—Laboratory Manual—Vol3, $2^{nd}$ ed." Sambrook, Fritsch, Maniatis; ppE10-15; Coldspring Harbour Press; 1989). We have however developed a method that enables ethanol to be added to a DNA solution to make it suitable for EHD.

DNA is usually stored with various buffer solutions which contain the salts of various chemicals. In this method, the vast majority of these salts are removed by dialysis to produce a relatively pure DNA solution. After removal of these salts ethanol is added to produce a formulation which is 80% by volume of ethanol. Surprisingly this does not cause the DNA to precipitate out. The reservoir of a dispensing device such as that shown in FIG. 1 or 2 was then filled with the formulation and the dispensing device activated. The liquid was sprayed at a flow rate of 1 μl/s (micro litre per second) from, in this example, a liquid supply tube in the form of a single capillary tube nozzle. This formulation was found to spray satisfactorily when the DNA concentration was low (up to about 200 micro grammes per millilitre) but did not spray satisfactorily at higher concentrations of DNA.

Further experiments were carried out with an ethanol concentration of 70% and different ethanol concentrations up to 90%. All were found to spray satisfactorily with low DNA concentrations.

Method 2

Method 1 was repeated but with the modification that a small amount (approximately 1 mM) of acetic acid was added to the formulation and sprayed at a flow rate of 0.5 ml/hr (millilitres per hour). This formulation was found to spray satisfactorily even when the DNA concentration was significantly increased and satisfactory spraying was achieved with DNA concentrations of 6 mg/ml. Similar results were obtained with acetic acid concentrations from 0.2 mM up to 1 mM (milli Molar).

Figure 5:
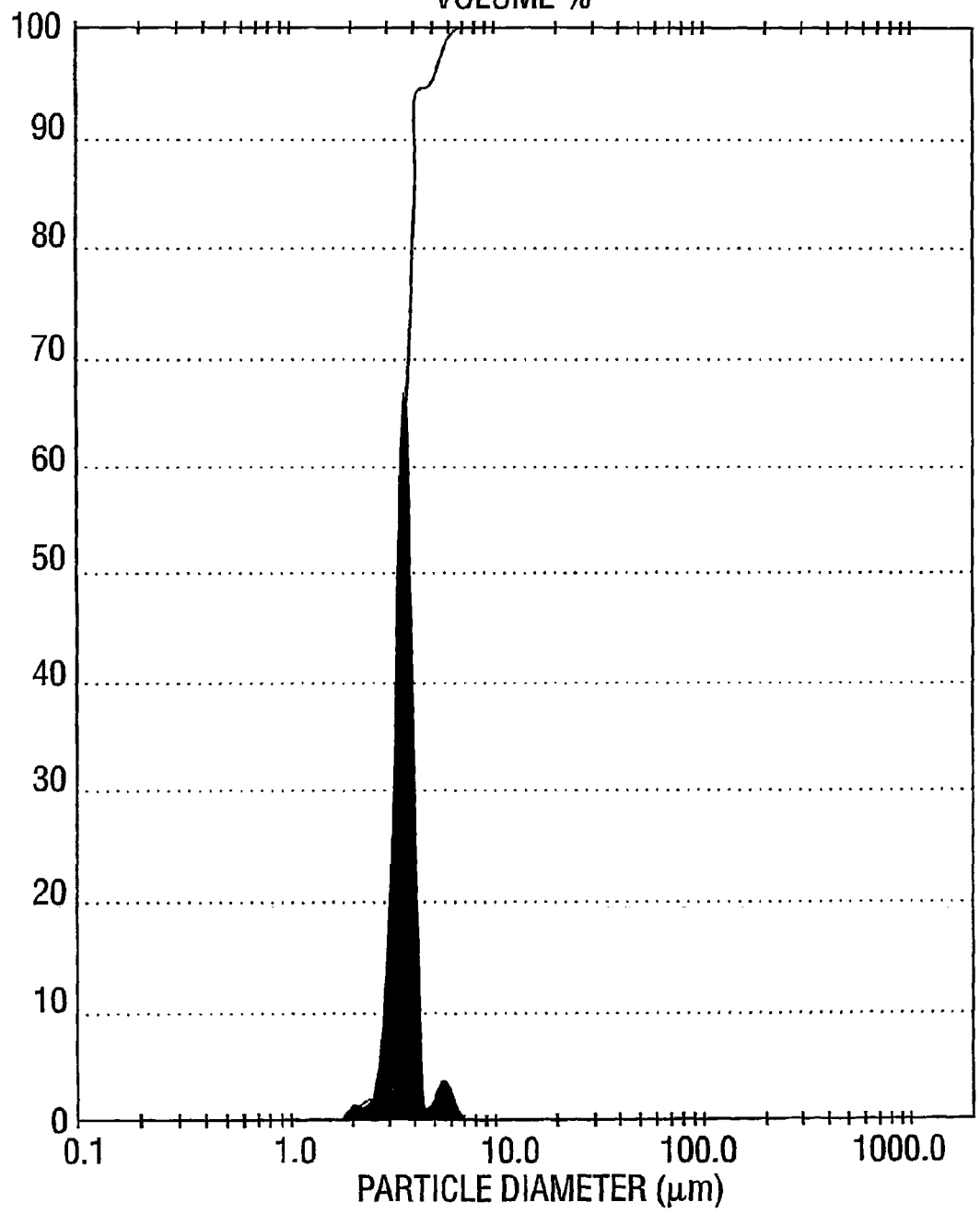
FIG. 5 shows the droplet spectrum obtained using a method embodying the present invention.

A practical rate of DNA nebulization was achieved without the precipitation any conventional formulation with this concentration of DNA would have caused. Also, the resulting EHD comminution had, as shown in FIG. 5, a very desirable droplet spectrum with a very narrow range of droplet diameters.

We have found acetic acid to be perfectly adequate for this purpose, but other acids have been used such as nitric acid and hydrochloric acid. This formulation enables spraying of DNA but can also be used for any proteins that do not denature in the presence of ethanol.

FIG. 6 shows a electrophoretic gel plot for various DNA samples after spraying through different nebulizers. The outer two lanes show the kilobase markers (Kb) that help quantify the results. The lane marked pCIKβGal shows the plot for the DNA that has not been sprayed. The lanes marked 'Jet' and 'Ultra' correspond to the DNA collected after nebulization with a 'Sidestream' air-jet nebulizer (produced by Medic Aid, of Bognor Regis, UK) and with a 'Euroneb' ultra-sonic nebulizer (produced by Medikare, of Germany). The smear of DNA below the original position (indicated by the pCIKβGal lane) in the Jet and Ultra lanes shows that the nebulization process resulted in significant damage to the DNA. By contrast the lane marked 'EHD' which shows the DNA dispensed using method 2 described above is practically identical to the original DNA, indicating little or no damage by the nebulization process. This also shows that the high voltages used during EHD comminution do not affect the DNA.

FIG. 7 shows plots similar to FIG. 6 of results obtained using method 2 for various different DNA plasmids. The results are grouped in pairs, where the left hand result for each pair represents the DNA before spraying whilst the right-hand plot shows the DNA after EHD comminution using method 2 described above. The three plasmids shown are pCIKCAT which is 4.6 kilobases, pCIKCFTR.10 which is 9.2 kilobases, and pREP8βGal which is 14.2 kilobases. As can been seen dispensing the DNA using method 2 above does not appear to affect any of these plasmids.

Methods 1 and 2 may be used to spray by EHD DNA, DNA fragments and other biological material that is not denatured by alcohols.

Method 3

In method 1 or 2, hydrogen peroxide is formed when ions created during the EHD comminution process react with the water in the formulation. Although the amount of hydrogen peroxide produced is extremely small, degradation caused by the peroxide can clearly be seen on the DNA. This degradation reaction is catalysed by the presence of metal ions in the formulation which are naturally present in minute quantities and are extremely difficult to get rid of. The amount of degradation is absolute and small and at DNA concentrations above 0.025 mg/ml, we have found that the percentage degradation is hardly noticeable. Consequently, for a therapeutic formulation, which might have a concentration 40 times greater than this or even more, the peroxide degradation can be neglected. However, where the concentration of DNA being sprayed is low, for instance around 0.0025 mg/ml, the effect on the DNA is significant.

In this method the formulation of method 1 or 2 was modified by adding either 50 mM ethylenediaminetetra-acetic acid (EDTA) or 40 nM Catalase.

Figure 8:
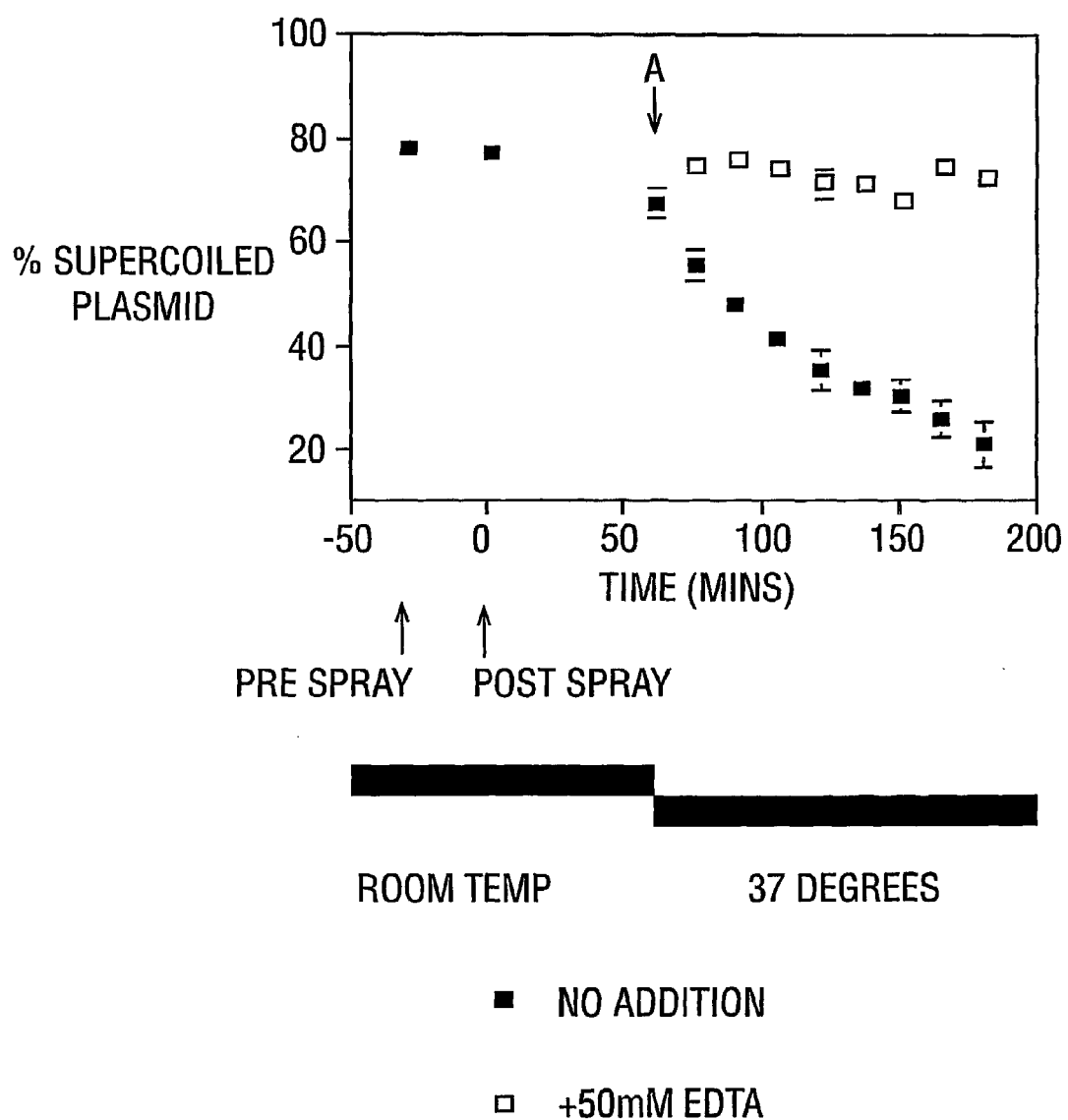
FIGS. 8 and 9 show graphs illustrating the effect on hydrogen peroxide degradation of the addition of EDTA and Catalase, respectively.
Figure 9:
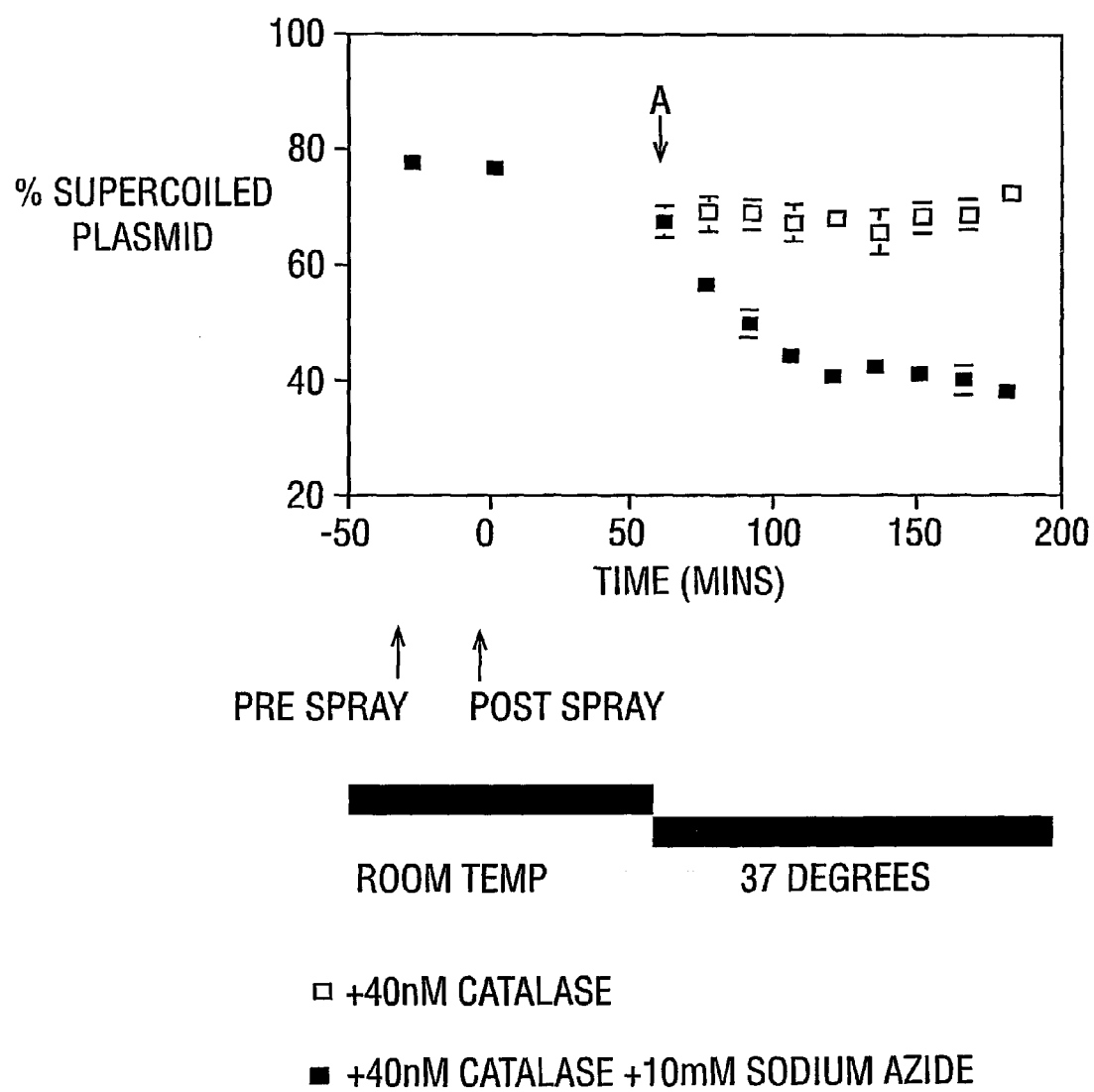

FIGS. 8 and 9 show the percentage of supercoiled DNA (determined by electrophoretic plot) in comminuted matter containing DNA collected after spraying using a formulation incorporating as an additive 50 mM ethylenediaminetetraacetic acid (EDTA) or 40 nM Catalase, respectively. Values are taken before and after spraying and for each formulation there is very little immediate damage, that is very little change in the amount of supercoiled DNA. However, at a time about one hour after spraying the results begin to diverge. Thus although the amount of supercoiled DNA in the collected comminuted matter produced using method 3 (shown by the solid squares) remains virtually unchanged, the amount of supercoiled DNA remaining in the collected comminuted matter which does not incorporate the additive (shown by the open or outline squares) begins to decrease. It is thus clear that the DNA sprayed without using the additive gradually deteriorates.

Although, as stated above, the amount of degradation is negligibly small at high DNA concentrations so that method 3 is not necessary at high DNA concentrations, where only low concentrations of DNA are wanted the results show that DNA degradation can be completely avoided by addition of a chelating agent such as EDTA or an enzyme such as catalase.

Further experiments involving the spraying of proteins have also been carried out and have proved that such molecules are also not denatured during EHD comminution. For example, Trypsin, peroxidase and recombinant lung surfactant-protein D have all been sprayed without denaturation. Also other alcohols than ethanol, for example polyethylene glycol 200 have been used.

Methods 1 to 3 may be used for any proteins or other biological materials that do not denature in ethanol or other alcohol eg polyethylene glycol 200.

Method 4

The introduction of ethanol or other co-solvents such as polyethylene glycol 200 may in some circumstances cause denaturation and may therefore be unacceptable.

This method provides another way of enabling comminution by EHD of aqueous formulations which may contain biological material. Until now it has been practically impossible to use EHD to comminute aqueous formulations. This is due to the high surface tension and high conductivity of these formulations which tend to cause the air to break down in the vicinity of the comminution point or region, leading to large, sporadic, local electrical currents, which generally cause catastrophic failure of the EHD cone-jet.

Where possible surfactants can be added to the aqueous formulation solution to lower the surface tension. All surfactants have an intrinsic property known as the Critical Micelle Concentration (CMC) which is the concentration at which micelles form in the body of the liquid, and which conventionally corresponds to the minimum concentration at which the surface activity of the surfactant is maximised. However, experiments have shown that this concentration is too little surfactant for EHD comminution, rather we have found that the concentration must be increased to allow for a monolayer distributed over the high specific surface of the comminuted matter in addition to the surfactant's CMC.

Experiments have been carried out using as the surfactant didodecyldimethylammonium bromide whose molecular surface area is roughly 68 $Å^2$. The Critical Micelle Concentration (approximately 0.061% by mass) was insufficient to produce satisfactory comminution using the dispensing device shown in FIG. 1 or 2. However increasing the surfactant concentration to a level sufficient to provide a monolayer coating enabled satisfactory comminution. Thus for typical droplets of 1.5 μm in diameter at least approximately 0.4% of didodecyldimethylammonium bromide is required and a concentration of around 0.5% was effective to produce satisfactory EHD comminution or spraying of the aqueous formulation.

Also we have found that addition of 0.1% benzalkonium chloride in water allows a liquid with a resistivity measuring only ~60 Ohm.m to spray at 0.12 μl/s. Similarly, addition of 0.8% Tween 20 (a polyoxyethylene sorbitan derivative) allows a liquid with a higher resistivity of approximately 625 Ohm.m to spray at the same flow rate.

Other suitable surfactants have also been used such as Tween 80, Emulphogen (now known as Rhodosurf BC720 (polyoxyethylene 10 cetyl ether)) Brij 30 (polyoxyetbylene 4 lauryl ether).

Method 5

Unfortunately, despite these results there are still some problems associated with using surfactants. These problems include: toxicity or irritation caused by the surfactants on sensitive epithelia; the fact the maximum flow rates are relatively low which leads to protracted treatment times; the relative instability of these sprays such that the cone-jet can easily be disrupted by mechanical vibration; and the fact that surfactants, in practice, generally only enable EHD sprays of a positive polarity—at negative polarity air breaks down more easily and the reduction of surface tension is generally not sufficient to allow spraying by EHD.

In this method higher flow rates can be achieved with conductive formulations containing biological material without the need for surfactants. In this method a long-chain polymer that is soluble in the liquid to be sprayed is added to the formulation. Where that liquid is water, suitable polymers include polyvinyl alcohol (PVA) and polyvinyl pyrrolidone (PVP), polyhyaluronate, polysucrose, and other polysaccarides, such as starch, cellulose and chitin and chemical derivatives thereof, poly amino acids, modified collagen and its derivatives. Other polymers that are, or can be made to be soluble in the liquid formulation (water soluble where the formulation is an aqueous formulation) may be used provided they are of a suitable length to effect the dynamic relaxation constant of the liquid. Also combinations of polymers or different weights of the same polymer may be used. For example PVP 40000 may be used in combination with PVP 360000 in the spraying of aqueous formulations.

As an experiment a highly conductive aqueous formulation with a resistivity of around 5 Ohm m was selected as the liquid to be sprayed. The surface tension of the liquid was roughly 70 mN/m and without formulation modification this liquid would not spray in air using EHD comminution. In this experiment, the aqueous formulation was found to spray satisfactorily at flow rates of up to around 1.5 ml/hour upon addition of only 2% of PVP of molecular weight 360000.

The molecular weight of the selected polymers is important because the benefits polymers such as these can provide will only be apparent if the molecular weight is suitably high. We have found that different polymers require different molecular weights and that the beneficial effects change gradually as higher molecular weights are selected. As a general rule, the higher the molecular weight of a given polymer, the lower the concentration needed to optimally modify a formulation for spraying. As the concentration of the polymer is increased, the product of comminution changes from being droplets to being fibres. The concentration at which this transition takes place illustrates the variation in effect that can be expected from different polymer types. As an example of using different molecular weights of the same polymer, formulations of ethanol containing PVP360000 in increasing concentration were sprayed and compared with ethanol formulations containing PVP40000. The formulations containing PVP360000 began to produce fibres at a concentration of 35 mg/ml, whereas the transition for the PVP40000 containing solutions was at 260 mg/ml. It follows, therefore, that less PVP360000 than PVP40000 would be needed to stabilise a given formulation. As an example of using different polymers, a formulation containing 70% Ethanol and 30% salty water (water containing NaCl at 0.5M) was sprayed with PVP 360000 and PVA125000 respectively. With PVP360000, the transition concentration of polymer was 55 mg/ml. With PVA125000, the transition from droplets to fibres occurred at a concentration of 30 mg/ml. Similarly, it has been shown that combinations of different molecular weight polymers follow the pattern. For example, a formulation containing 70% Ethanol and 30% salty water (water containing NaCl at 0.5M) was sprayed containing both PVP40000 and PVP360000 (in 50:50 ratio), the transition concentration of combined polymer in this case was 70 mg/ml.

Figure 10:
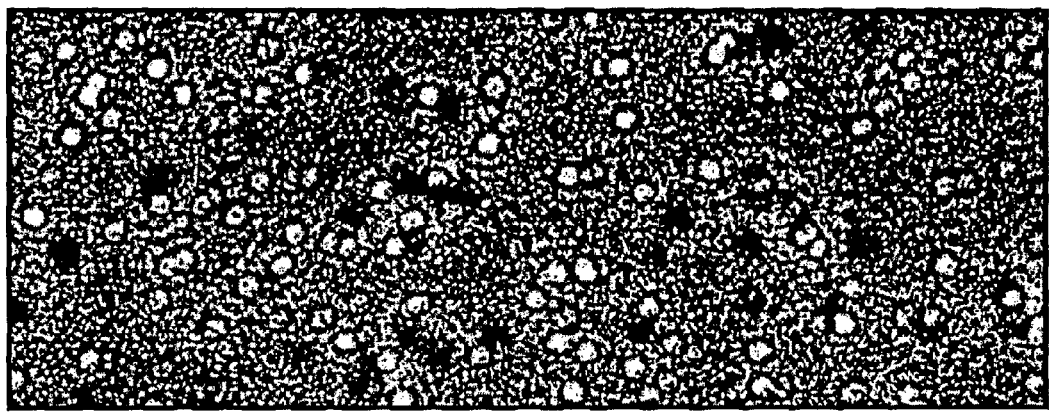
FIG. 10 shows a photograph of an example of comminuted matter produced using a method embodying the invention.

In another experiment a formulation was used which consisted of 70% ethanol, and 30% water. The water also contained some salt (NaCl) at 0.5M to mimic the effect of adding an active molecule, biological material or drug, lowering the resistivity to 4.7 Ohm.m. 0.2 g/10 ml PVP of molecular weight 360000 was added to the formulation which was sprayed using a device such as that shown in FIG. 1 or 2. FIG. 10 shows a close up photograph taken from a microscope slide on which the resultant comminuted material was collected. The droplets formed are of a respirable size, measuring roughly 5 μm or below. The vertical dimension of the photograph is 75 μm.

Figure 11:
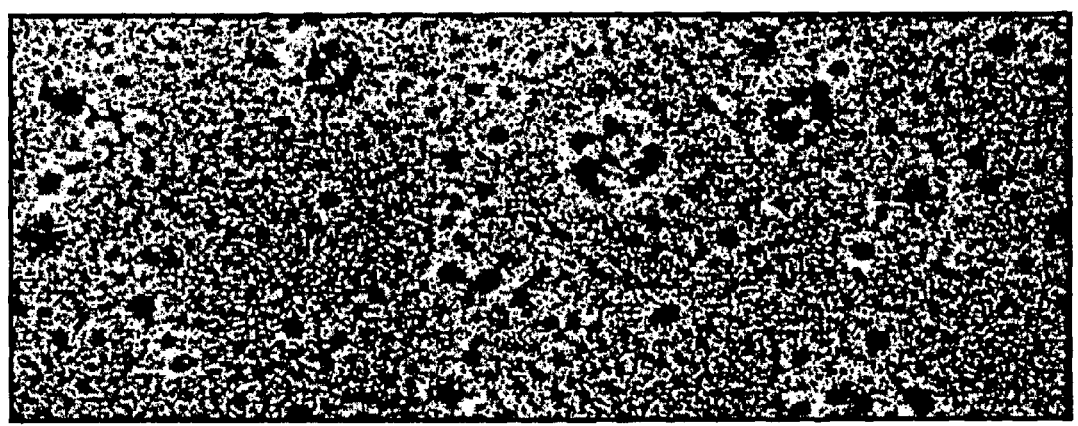
FIG. 11 shows a photograph of another example of comminuted matter produced using a method embodying the invention.

In another experiment 10 mg/ml of PVA of molecular weight 125000 was added to a formulation containing 70% ethanol and 30% water by volume, where the water contained 0.5M salt (NaCl) and the formulation had a resistivity of 5.5 Ohm m. FIG. 11 shows a picture similar to FIG. 10 taken from a microscope slide on which the resultant comminuted material was collected. Again the vertical dimension of the photograph is 75 μm and the droplets produced were respirable.

Similar results were obtained with PVA of molecular weight 125000 in concentrations of 0.1, 0.2, 0.3, 0.4, 0.5, 0.6 and 0.7 grammes per 10 millilitres of liquid formulation and with PVP of molecular weight 360000 in concentrations of 0.2, 0.4, 0.6, 0.8, 1.0 and 1.2 grammes per 10 millilitres of liquid formulation consisting of 70% ethanol and 30% 0.5 Mol water-NaCl solution to mimic the presence of an active ingredient in the form of biological material. Similar results have also been obtained by adding a polymer combination of 50% PVP of molecular weight 40000 and 50% PVP of molecular weight 360000 in concentrations in the range 0.5 g/10 ml to 0.8 g/10 ml of formulation. Concentrations of polymers above a certain level will result in fibre formation rather than droplets formation with the actual level being dependent on the polymer and the formulation. Typically this level is about 0.5 g/10 ml for PVP 360000, 0.6 g/10 ml for a 50:50 mix of PVP of molecular weights 40000 and 360000 and 0.25 g/10 ml for PVA of molecular weight 125000.

Incorporation of a long chain polymer enables in a dynamic reduction of the formulation's relaxation constant to be achieved allowing higher flow rates with conductive liquids. Furthermore, and more importantly, the polymer-incorporating liquids will spray at either polarity.

Method 6

In this method, a combination of polymer and surfactant is used to optimise the EHD spray and electrosol product.

A formulation consisting of a solution of salt (NaCl) dissolved in water at 0.5M was used as an example. This will not spray using EHD comminution. However, after adding 1.7% (17 mg/ml) PVA with a molecular weight of 125000 and 1% (10 mg/ml) Tween 20, the formulation (whose properties were: resistivity=4.3 Wm; surface tension=32 mN/m; and viscosity=13 cP) sprayed at flow rates between 0.2 and 0.6 ml/hour.

Similar results may be obtained with any of the polymers mentioned above.

Method 7

Our experiments have shown that delicate molecules such as proteins can be stabilized by the addition of polymers.

In this method, various proteins were conjugated with polyethylene glycol (PEG) prior to spraying. This was found to increase their stability, to protect the proteins from mechanical stresses and to enable them to tolerate more variation in their liquid carrier or vehicle. Other polymers having properties similar to PEG produce similar results.

Examples of experiments carried out to spray trypsin, peroxidase and insulin will now be described.

Clinically available proteins such as insulin and growth hormone are currently delivered by injection, and cannot be administered by the oral route, since they are digested and inactivated in the gastrointestinal tract and a significant portion are metabolised in the liver. It is therefore important to develop a pulmonary delivery system to enable a wide range of these proteins to be delivered to the lungs. Insulin was used to determine the effects of spraying proteins with EHD technology.

Enzymes are essential in all cells, and belong to a large and diverse group of proteins. They function as biological catalysts in virtually all biochemical reactions in biological systems. Trypsin is a proteolytic digestive enzyme that found in pancreatic juice of mammals. Peroxidase is another type of enzyme that presents in plants and animals, especially mammalian spleen and lung, which acts on hydrogen peroxide and organic peroxides. These two enzymes were therefore used, as model systems, to determine the effects of spraying proteins with EHD technology.

Method 8

Examples of formulations using PEG200 will now be described.

Trypsin

Trypsin was first dissolved in sodium phosphate ($NaPO_4$) buffer and then formulated with PEG200 to make the final formulation: trypsin in 20% sodium phosphate 80% PEG200. 100 μl of this formulation was sprayed into a 35 mm polystyrene tissue culture dish containing 2 ml $NaPO_4$ buffer, with a flow rate of 1.5 μl/sec at +12.1 kV. A platinum loop immersed in the $NaPO_4$ buffer was used as the earth. After spraying the trypsin/$NaPO_4$ solution was removed by pipette from the culture dish for enzyme assaying immediately after spraying, and 1, 2, 3, 4 and 5 days later. The whole experiment was repeated four times and results showed that 99.53% of the trypsin activity was retained after spraying. Therefore, it is concluded that the EHD spraying technique (without discharging in this example) does not result in loss of enzyme activity when PEG200 is incorporated in the trypsin formulation.

Peroxidase

Peroxidase was formulated in 20% peroxidase diluent (containing potassium phosphate buffer, bovine serum albumin and triton X-100) and 80% PEG200. As with trypsin, 100 μl of this formulation was sprayed into a tissue culture dish containing 2 ml peroxidase diluent, with a flow rate of 1 μl/sec at +11.9 kV. Again, a platinum loop immersed in the peroxidase diluent was used as the earth. Based on a single experiment, >90% of the peroxidase activity was retained four days after spraying with the EHD technique (without discharging).

PEG (polyethylene glycol) can thus be used to stabilise proteins to facilitate EHD.

Method 9

A method of enabling EHD spraying of formulations containing alcohol and biological material will be described.

Addition of PEG200 has, as set out above been shown to increase the stability of proteins; however, in terms of toxicity, 80% PEG200 in the formulation is a high level for inhalation, therefore alternative solvents were considered. To this end, trypsin and peroxidase were formulated with propylene glycol (often used in conjunction with water or glycerol). Also, to determine if ethanol could be a potential solvent for spraying enzymes, formulations containing ethanol were also tested.

Trypsin was formulated in:
a) 20% $NaPO_4$ buffer, 80% propylene glycol [sprayable with flow rates of 0.6-2.4 μl/sec at voltages of +(8.1-8.6) kV],
b) 20% $NaPO_4$ buffer, 40% propylene glycol, 40% ethanol [sprayable with flow rates of 0.6-1 μl/sec at +8.32 kV],
c) 20% $NaPO_4$ buffer, 60% propylene glycol, 20% ethanol [sprayable with flow rates of 0.6-1 μl/sec at voltages of +(7.42-7.62) kV,].

Solutions (b) and (c) turned milky immediately after they were made.

Peroxidase was formulated in:
d) 20% peroxidase diluent 80% propylene glycol [sprayable with flow rates of 0.6 μl/sec at +9.5 kV],
e) 20% peroxidase diluent, 40% propylene glycol, 40% ethanol,
f) 20% peroxidase diluent, 60% propylene glycol, 20% ethanol.

Solutions (e) and (f) were only sprayable with flow rates of 0.01-0.02 μl/sec; corona resulted when the flow rate was higher. The solutions turned milky immediately after they were made.

Proteins are usually dissolved in buffer solutions that contain salts of various chemicals. Solutions turned milky when they were formulated with alcohol, suggesting that precipitation of salts by the alcohol might have occurred. Results from a preliminary experiment showed that phosphate buffer solution indeed turned milky when alcohol was added. Also, a trypsin assay (see Appendix) was performed to test whether the enzyme was stable after mixing with alcohol. The enzyme activity was determined at 0, 1.5, 3, 4.5 and 6 hours after formulation. Results showed that at each time point, similar enzyme activity was detected in formulations containing 20% sodium phosphate buffer and 80% PEG 2000, and 20% sodium phosphate buffer and 80% ethanol, when compared with the formulations containing sodium phosphate buffer only. These results show that the activity was retained in formulations containing alcohol.

Method 10

A method of spraying insulin by EHD will now be described.

Porcine insulin was formulated with three different formulations:

7. 0.5% Emulphogen, 5% sodium phosphate ($NaPO_4$) buffer, 30% glycerol and 64.5% water
8. 0.2% 0.01 M HCl, 19.8% sodium phosphate buffer and 80% PEG200
9. 20% 0.01 M HCl and 80% PEG200

100 μl of each formulation was sprayed into a 35-mm polystyrene tissue culture dish containing 2 ml $NaPO_4$ buffer. A platinum loop immersed in the $NaPO_4$ buffer was used as the earth. After spraying, the insulin/NaPO$_4$ solution was removed by pipette from the culture dish for insulin testing with the ELISA method.

Results:

| Formulation | Flow rate | Voltage |
|---|---|---|
| 0.5% Emulphogen<br>5% sodium phosphate buffer<br>30% glycerol<br>64.5% water | 0.22 µl/sec | +6.6 kV |
| 0.2% 0.01 M HCl*<br>19.8% sodium phosphate buffer<br>80% PEG200 | 1 µl/sec | +9.54 kV |
| 20% 0.01 M HCl<br>80% PEG200 | 1 µl/sec | +9.24 kV |

It was thus found that insulin can be formulated in three different sprayable formulations. The activity of insulin after spraying was determined by the ELISA method.

Trypsin, peroxidase and insulin can thus be delivered using EHD in various formulations.

Other Methods

Experiments have been also carried out to spray surfactant proteins using EHD. Pulmonary surfactant plays an important role in lowering the surface tension at the alveolar epithelial lining, by preventing the collapse of alveoli during gas exchange. Failure or deficiency of these proteins is associated with respiratory diseases such as respiratory distress syndrome (RDS). RDS remains the most common cause of neonatal mortality. The administration of exogenous surfactant to newborn infants who have RDS is becoming an established therapeutic approach.

Allergic reactions triggered by pollen grain/dust mites, and lung infections caused by respiratory syncytial virus (RSV) are significant problems worldwide. So far, no safe and efficient drugs are available for the prevention or treatment of these diseases. There is strong evidence that the lung surfactants (SPs), such as SP-A and SP-D, are involved in innate immunity, in which they bind to and remove allergens such as pollen, house dust mite droppings and pathogens such as viruses and fungi.

There are two main types of exogenous surfactant proteins currently available—natural and synthetic. Natural surfactants are obtained from animals or humans by means of alveolar wash or from amniotic fluid. They have the advantage of having all the necessary ingredients for effective function to regulate surface tension; however, their collection is not time and cost effective. Also, they carry a risk of contamination with infectious viral agents. On clinical grounds, natural surfactants have greater efficacy than synthetic ones, perhaps due to the protein content of natural surfactants. Therefore, recombinant lung surfactant proteins were developed and these sensitive molecules can be delivered to the lungs for prevention and treatment of respiratory diseases, such as bronchial asthma, bronchiolitis and pneumonia, and enhancement of the immune defence in lung transplants.

The current method used to deliver proteins to the lungs of, for example, mice is an invasive technique—intra tracheal instillation. In this method, hypodermic needles are inserted into the trachea of mice, through which proteins are delivered to the lungs. The insertion of hypodermic needles to the trachea can easily damage the surrounding tissues, which might elicit unnecessary immune responses in the mice. Also, protein solutions delivered by the intra tracheal instillation are not administered as droplets, but probably in aggregated form. Therefore, proteins are unlikely to reach the lower respiratory tract.

Another way to deliver proteins is by using liquid droppers, whereby proteins are delivered intra-nasally to animals such as mice. Similar to the intra tracheal instillation, one significant drawback of this delivery method is that it cannot deliver proteins accurately and therefore results in an inefficient transferring of proteins.

In contrast to intra tracheal instillation, EHD enables material to be delivered gently to the lungs of mice and humans, without damaging the tissue along the respiratory tract. EHD also enables accurate delivery of material because the size of the electrosol can be well-controlled and so set to optimise the deposition zone in the lungs in dependence on the mass and shape of the droplets. For example EHD may be used, as can be seen from FIG. 5, to produce a monodispersed droplet spray in which the droplets all have substantially the same diameter with that diameter having a value in the range 1.0 to 10 microns for humans and proportionally smaller for smaller animals. In addition EHD enables the resultant droplets to be electrically charged, electrically discharged or partially electrically discharged as described in at least some of the patents and published applications mentioned above and retention of a small electrical charge may be advantageous, particularly for deposition in the terminal airways and alveoli.

Examples of EHD spraying of surfactant proteins

Recombinant SP-D (rSP-D) protein was formulated in three formulations (a), (i) and (j) for spraying by EHD using the device as disclosed in WO 99/07478. The further electrode was at earth (ground) potential. The formulation details and maximum flow rates obtainable were:

| Formulation | Flow rate, (ml/h) | Discharge electrode voltage (kV) | First electrode Voltage (kV) |
|---|---|---|---|
| (a) 3% PVA (100 k in mol wt), 1% Tween 20, 96% 0.5 M NaCl | 1.7 | 2.36 | −2.89 |
| (i) 2% PVA (100 k in mol wt), 1% Tween 20, 48.5% 0.5 M NaCl, 48.5% glycerol | 7.25 | 2.95 | −3.26 |
| (j) 2% PVA (100 k in mol wt), 1% Tween 20, 48.5% 0.5 M NaCl, 48.5% PEG200 | 2 | 3.03 | −3.08 |

The three formulations (a), (i) and (j) were tested for their effect on the SP-D molecule without spraying. Recombinant SP-D was added to each of the samples and assayed to test activity in each formulation, run against a control sample, Eagan 4A. A graph showing the activities of each mixture is shown as FIG. 23. The activity of the rSP-D in the formulations (a), and (j) was only slightly reduced. However, the SP-D in the formulation (i) did not produce a positive signal. It was not proven whether the glycerol actually denatured the rSP-D or simply interfered with the assay mechanism.

rSP-D in Aqueous Formulation

Based on the success with aqueous PVA and surfactant formulations described above, 0.1 mg/ml of rSP-D protein was formulated in 3% PVA (100 k in mol wt), 0.1% Tween 20 and 96.9% PBS. This formulation was sprayed at a flow rate of 1 ml/hr. The spraying was performed as a simple point-to-plane (nozzle tip to collection surface) experiment, using a device similar to that shown in FIG. 1 but without the second electrode and using as the liquid supply tube or nozzle a Delrin tip with no central vane. The spray was collected in a petri dish using an earthed platinum wire loop. The point-to-plane distance was 20 mm. Dead space was minimized, using 1 ml syringes and IV tubing, to conserve the sample since two repeats were performed for each formulation. A bioassay was performed to determine whether the proteins remain fully active, or denatured by the shear forces of the EHD process. Results showed that no adverse effects on the rSP-D due to EHD spraying occurred.

EHD spraying of SP-A and SP-D in vitro has also been achieved with a near mono-dispersed spray or cloud being formed and no denaturing. Controlled droplet charge has also been achieved by the use of a twin nozzle EHD device as described in WO 94/12285, the whole contents of which are hereby incorporated by reference.

The above described experiments have shown that delicate materials such as biological material, for example DNA, proteins and enzymes, can be subjected to electrohydrodynamic comminution without causing electric-field induced denaturation, because the liquid carriers or vehicles of the formulation to be sprayed are more conductive than conventional EHD formulations (i.e. have resistivities less than 10,000 Ohm.m or more preferably 1000 Ohm.m). This extra conductivity helps to reject the external electric fields and thus protects against electric-field induced denaturation. Also, the shear forces occurring during the EHD process are exceedingly low. The current wisdom is that the EHD cone which is the electric-field induced transition region between bulk liquid and comminuted electrosol is highly turbulent with a toroidal eddy current set up by the electric field (Hayati I, 1985—*Ph. D. Thesis, Imperial College London*). However, the amount of turbulence is related to the conductivity and viscosity of the liquid as well as the physical dimensions of the comminution region or point. The conductive formulations described here make a significant reduction to the shear forces exerted on the liquid, and these can be reduced further by increasing the viscosity or reducing the diameter of the base of the EHD cone. Overall, we calculate that the liquids used experience shear forces during the EHD process that are around 1000 times lower than air-jet and ultra-sonic nebulizers for the same size droplets.

The above methods may, as set out above, be implemented with an EHD dispensing device such as that shown in FIG. 1 or 2. This EHD device may, as will be described below, be incorporated into an inhalation apparatus that enables control over environmental conditions.

FIG. 12 shows schematically one example of an inhalation apparatus suitable for facilitating inhalation of droplets by small laboratory animals such as mice.

A pump 101 drives air through the inhalation apparatus at a constant rate. The air from the pump travels through an air adaptation unit 102 into an EHD comminution device or unit 103. The air and comminuted matter then travel into an inhalation chamber 104 where the small animals, generally mice, are placed to breathe the mist of droplets. Exhaust air exits via a filter 105 into the atmosphere.

In this example, the air adaptation unit 102 is designed to remove vapour from the incoming air.

Figure 16:
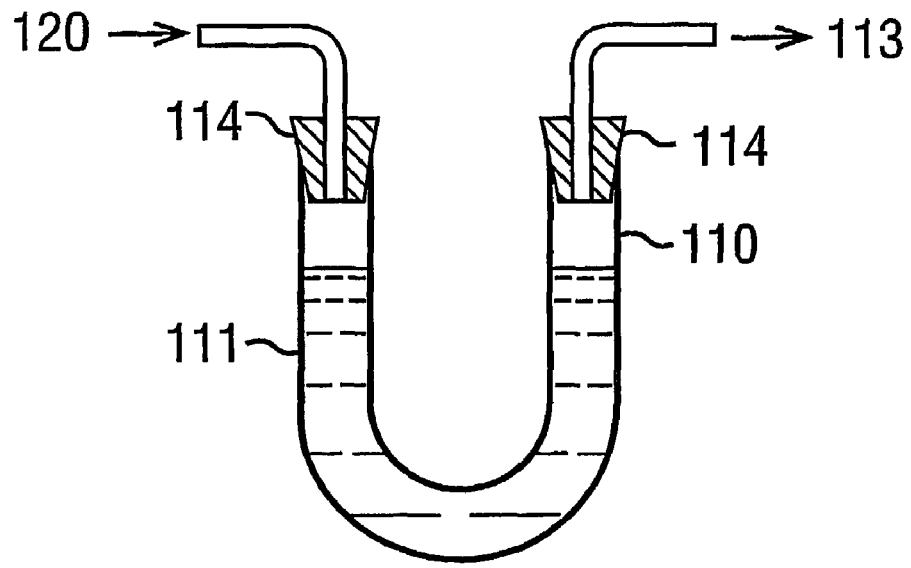
FIGS. 16 and 17 illustrate schematically and in cross-section different examples of air adaptation units suitable for use in an inhalation apparatus.

FIG. 16 shows a cross-sectional view of one possible air adaptation unit 102, which comprises a U-tube 110 filled with desiccated silica gel 111. Air flows in through an inlet port 120 of the U-tube, is forced to pass through the silica gel 111 held in the U-tube and exits though an exit port 113. Both inlet and exit ports are secured and made air tight by means of flexible bungs 114 made from rubber or another suitable material. In this way moisture is removed from the incoming air before it enters the EHD comminution unit 103. This enhances droplet evaporation enabling the production of smaller droplets. It will be evident to a person skilled in the art that other materials can be placed in the U-tube to remove gases and vapours to help reduce droplet size.

Figure 19:
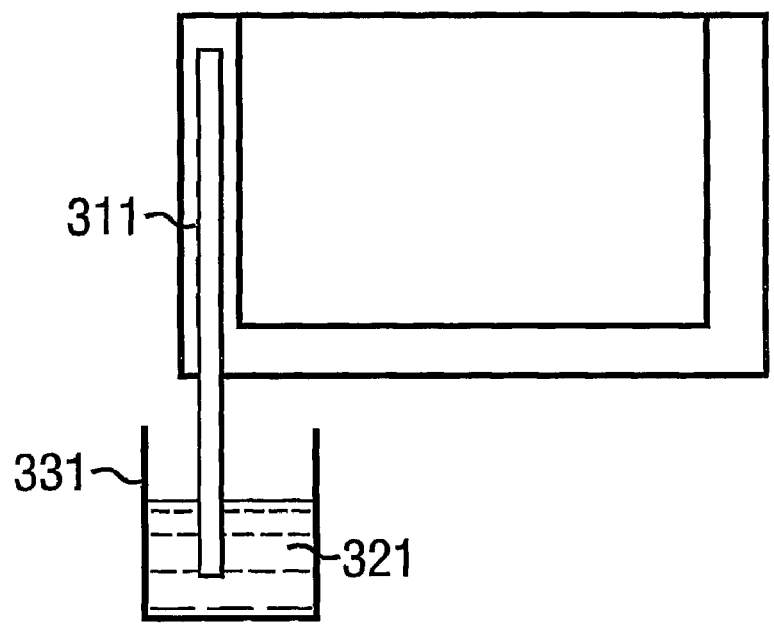
FIGS. 19 and 20 illustrate schematically two versions of cold traps that may be used as air adaptation units in an inhalation apparatus.
Figure 20:
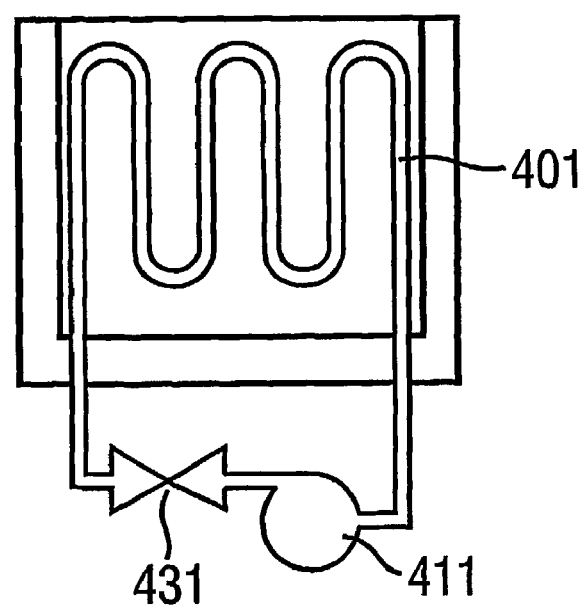

FIGS. 19 and 20 show two alternative cold traps which are suitable for use as the air adaptation unit 102 for the removal of vapour from the air. In FIG. 19 a metal rod 311 is inserted between the inner and outer chambers of the inhalation box 104. The rod is dipped into liquid nitrogen 321 or another very cold liquid or solid held in a beaker 331, so that the rod becomes very cold. The part of the rod protruding inside the inhalation box will condense out any vapour, and will significantly reduce the vapour concentration throughout the box by simple vapour diffusion. FIG. 20 shows an alternative cold trap which runs in a similar fashion to a household refrigerator. Here a suitable refrigerant such as Freon-12 (dichlorodifluoromethane) is pumped around a metal tube 401 by a compressor 411. The Freon-12 is allowed to expand across a valve 431 which significantly reduces its temperature and cools the metal tube. This inhalation apparatus can be adjusted during the experiment to automatically maintain a specific vapour concentration if coupled to a suitable monitoring device (not shown). Other suitable cold traps will be evident to a person skilled in the art.

Figure 15:
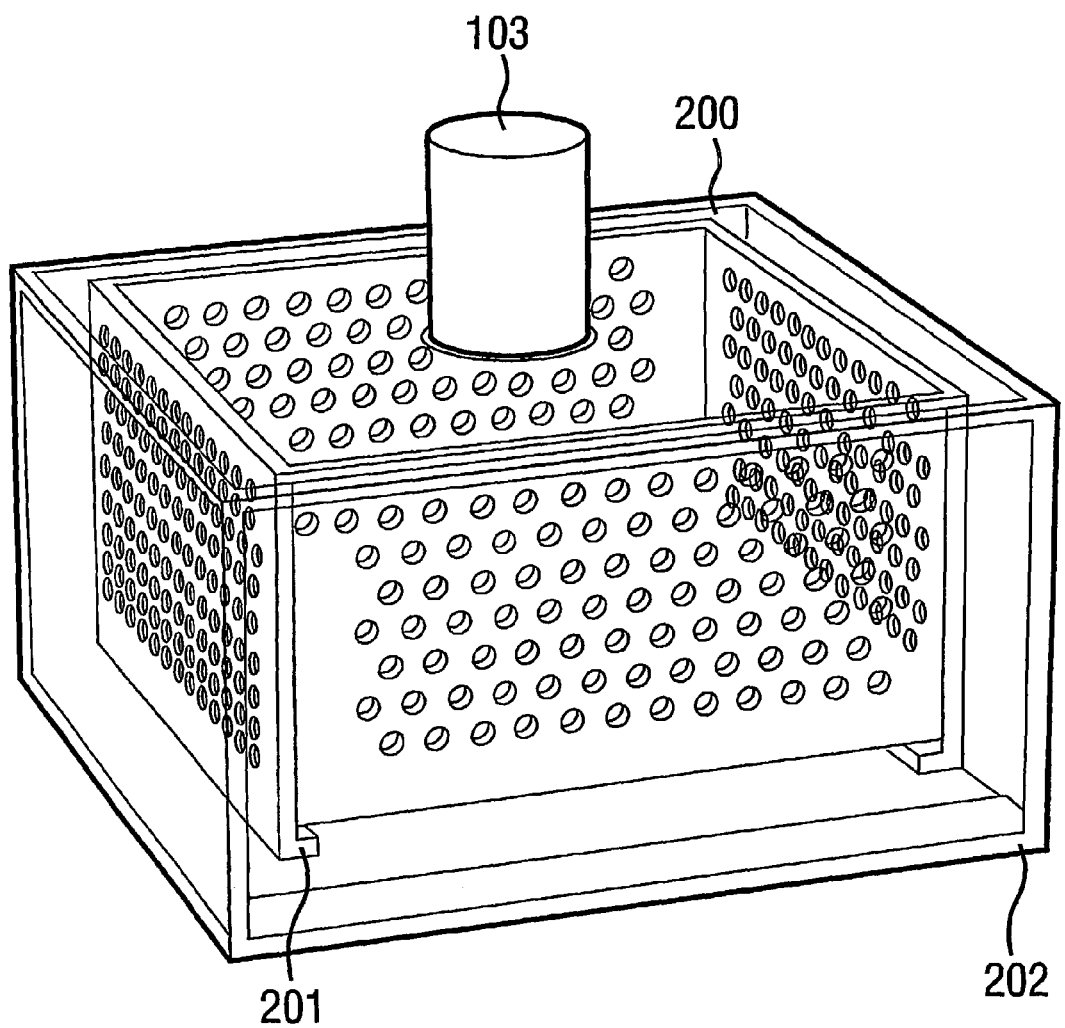
FIG. 15 shows a perspective view of an EHD comminution chamber and inhalation chamber suitable for use in the inhalation apparatus shown in FIG. 12.

FIG. 15 shows an example of a suitable inhalation chamber 104 for mice for use in the inhalation apparatus shown in FIG. 12. The chamber consists of a box 20 is made from Perspex having a perforate inner chamber 201 held symmetrically inside a sealed outer chamber 202 (apart from an air exhaust to which the filter 105 is coupled). The EHD comminution unit or device 103 is mounted in the centre of the box lid to direct comminuted material into the perforate inner chamber 201. The inhalation chamber 104 may have ambient modification means for modifying and controlling evaporation or absorption of droplets produced by the EHD comminution unit 103 to enhance evaporation from the droplets to facilitate droplet size reduction. The ambient modification means may be provided by placing absorbent material, such as silica gel or active charcoal, in the gap between the inner and outer chambers 201 and 202 to absorb any unwanted vapour from the inhalation chamber so as to promote evaporation from the surface of droplets produced by the EHD comminution unit to reduce their size.

Figure 18:
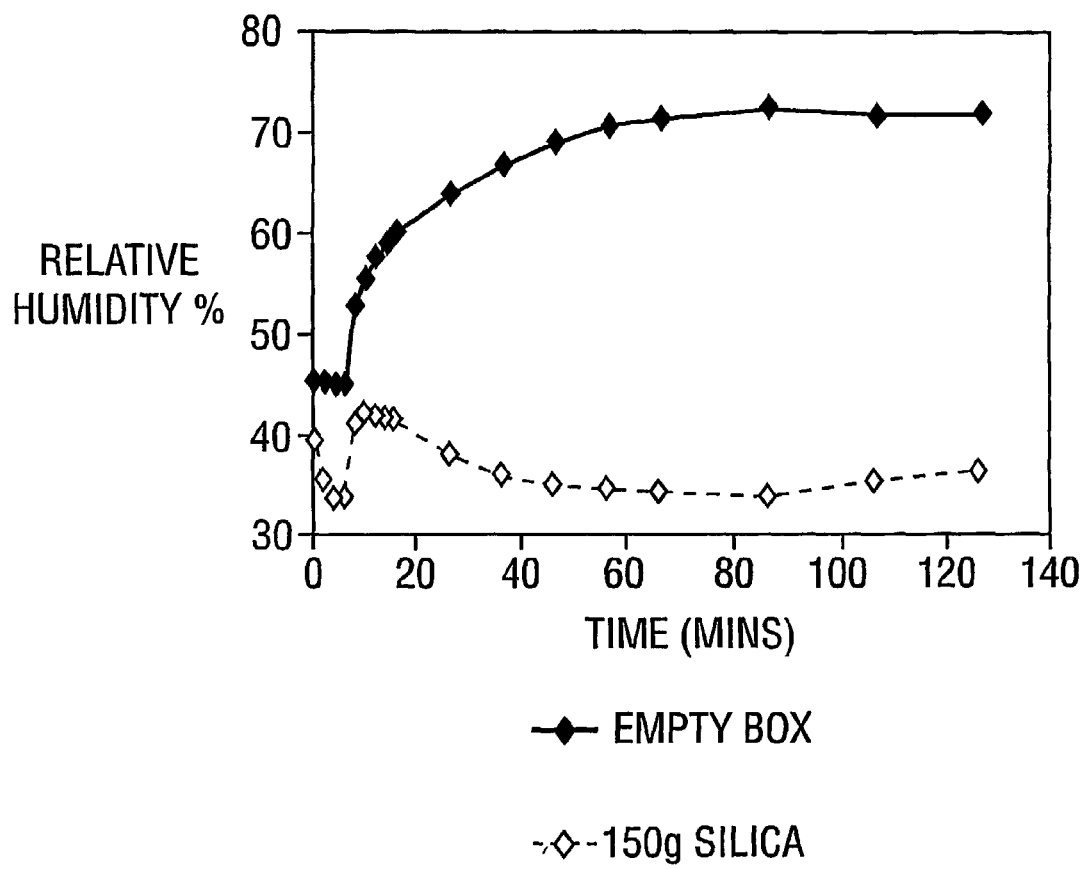
FIG. 18 shows a plot illustrating the change in humidity concentration in the inhalation chamber of the inhalation apparatus shown in FIG. 12 over time with and without the air adaptation unit.

FIG. 18 shows how the humidity of the inhalation chamber 104 can be radically altered over time by addition of 150 g of silica gel in the inhalation chamber. In this case the box was being sprayed with a 20% water, 80% ethanol mix by volume at a rate of 2.4 µl/s. It is clear from the graph that the presence of the silica gel ensures the relative humidity in the box does not rise much above 40% for the entire duration of the experiment. It should be noted, however, that this experiment was carried out with no animals in the box. Their breathing generates a substantial amount of water vapour, and so cold traps such as those shown in FIGS. 19 and 20 may be introduced in between the inner and outer chambers to remove water vapour and other vapours from the air inside the inhalation chamber 104.

Typical air flow rates for this inhalation apparatus can vary from 0 to 60 L/min and above, but are preferably as low as possible, whilst maintaining a suitable oxygen level in the inhalation chamber. In an experiment, ten mice were placed in the inhalation chamber 104, the pump was arranged to provide a flow rate of 4 l/min (litres/minute) of air and the EHED comminution unit 103 was arranged to spray a formulation as described above in Method 2 with a DNA concentration of 1 mg/ml at a flow rate of 2.4 µl/s. 17.3 mg of DNA was comminuted by the EHD comminution unit 103 over 2 hours and roughly 6 µg was retained in the lungs of the mice.

This inhalation apparatus offers a way of controlling the droplet diameter and charge accurately down to the sort of sizes suitable for mice (e.g. 1-3 µm and below). This inhalation apparatus therefore enables the production of respirable aerosols for mice and similar small laboratory animals which would otherwise be extremely difficult due to their small anatomy and non-compliant breathing facilitating the in vivo testing of the toxicity and activity of a therapy on animals such as mice (which have very different requirements from humans for inhalation due to their radically different anatomy) as the necessary precursor for any human pulmonary therapy.

The use of chambers for the forced respiration of aerosols is well known. However, conventional inhalation apparatus are inefficient in terms of the mass of product actually inhaled by the animal compared with the amount delivered. For instance, an air jet nebulizer which produces droplets of 1 µm, a suitable diameter for inhalation by mice, must be run at an air throughput of around 6-8 L/min (litre/minute). Consequently, it is difficult to build up a very high concentration of the aerosol in the air since it is continually diluted by the air creating the aerosol in the first place. By contrast, in the inhalation apparatus described above the EHD comminution unit 103 creates the droplets and only a relatively small air flow (<1 L/min) is required to maintain the oxygen concentration in the inhalation chamber 104. This means the electrosol can be concentrated by an order of magnitude, and thus the inhalation apparatus is an order of magnitude more efficient than with a conventional air jet nebulizer. Ultrasonic nebulizers can also be used without air flow. However, they also denature sensitive biological material; they cannot be used with viscous liquids, (such as concentrated solutions of DNA); and they easily block when creating droplets of around 1 µm.

FIG. 13 shows schematically an inhalation apparatus designed for use with larger animals or human beings. In this inhalation apparatus the inhalation chamber 104 is replaced by an intermediate chamber 106 plus either a mask 107 as shown, which can fit over the mouth and nose of a larger animal such as a human (for example as shown in FIG. 3) or a mouthpiece or intra tracheal tube. The mask can be any standard inhalation mask such as is available from Medic Aid, Bognor Regis, UK, Item Reference: 1100 System 22 face mask. The intermediate chamber 106 may be based on the inhalation chamber 104 shown in FIG. 15 and so may be provided with the modification means for modifying and controlling evaporation or absorption of droplets produced by the EHD comminution unit 103 prior to delivery to the mouthpiece or mask 107.

FIG. 14 shows schematically an example of an inhalation apparatus intended for use by human beings. In this case the EHD comminution unit, intermediate chamber and mask are replaced by a single EHD inhalation device 108, such as described in WO99/07478. It should be noted that this inhalation apparatus could function perfectly well without the pump 101 or air adaptation unit 102, although the use of the air adaptation unit may be advantageous to enable droplet size reduction as described above.

As described above the air adaptation unit 102 and possibly also the inhalation or intermediate chamber 104 or 106 are arranged to remove vapour from the ambient air to facilitate evaporation from droplet surfaces to reduce the droplet size. There are, however, circumstances where it may be desirable to increase the vapour pressure of a solvent or volatile component in the air in which or in the vicinity of which the EHD process takes place. For example the solvent vapour pressure may be increased to hinder evaporation to, for example, slow down or inhibit solidification of the liquid issuing from the outlet of the EHD comminution unit 103. This is particularly useful where the liquid formulation contains polymer because it enables solidification to be prevented and so allows droplet formation for higher polymer concentrations than would otherwise be possible.

Figure 17:
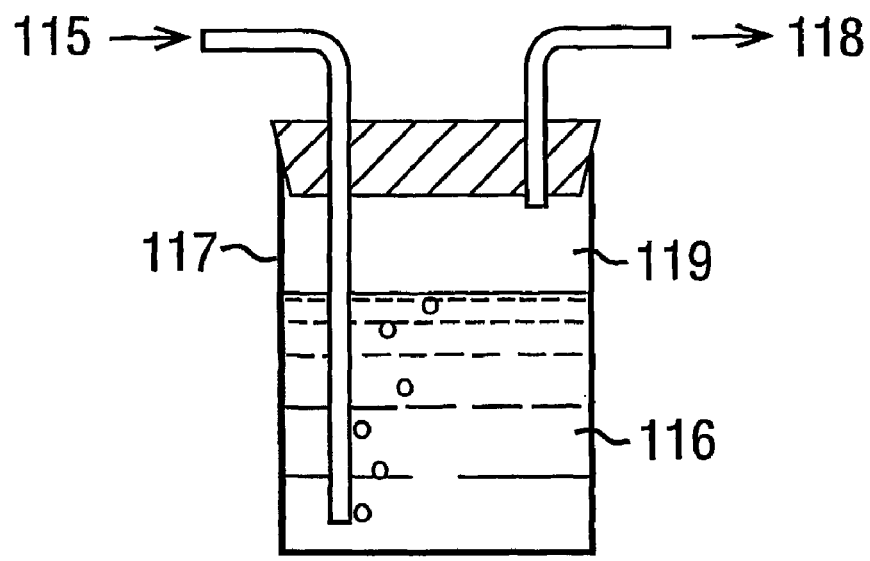

FIG. 17 shows a cross-sectional view of a bubble chamber which may be incorporated into the air adaptation unit 102 (and/or the inhalation or intermediate chamber) and can be used to increase the partial vapour pressure, for example saturate the air which enters the EHD comminution unit 103, with vapour of any solvent used in the liquid formulation. Referring to FIG. 17, air is pumped in through the inlet port 115 and bubbles through the liquid 116 which is held in a container 117. The air then exits through the exit port 118. Both ports are held in place by air tight bungs 119 made from rubber or other suitable material. Experiments have shown that an aqueous formulation containing a polymer can be prevented from drying out and forming a solid product by using such a bubble chamber containing as the liquid 116 warm water.

Where, as shown in FIG. 15, the EHD comminution device 103 is inserted into an inhalation or intermediate chamber, then the air adaptation unit 102 may be arranged to control the humidity of the air in that chamber rather than or in addition to in the EHD comminution device 103 so that a separate modification means is not necessary.

As described above the diameter of droplets formed by the EHD comminution unit 103 may be controlled by controlling the ambient in which the droplets are formed (by use of the air adaptation unit and/or by controlling the ambient in the inhalation or intermediate chamber 104 or 106 as described above). Thus the droplet size can be reduced by enhancing evaporation of water (or volatile component such as a solvent in the formulation, for example ethanol) from the droplets by decreasing the partial vapour pressure of the water (or volatile component) in the ambient. Thus drying the ambient air to reduce its humidity as described above will increase evaporation of water from the droplets and so reduce their size. Conversely increasing the humidity (using for example the bubble chamber shown in FIG. 17) or increasing the partial vapour pressure of a volatile component of the formulation would hinder evaporation and so hinder droplet size reduction. In addition, where the liquid formulation contains a substance that is hygroscopic, droplets can also take on water during flight and increase in diameter.

FIGS. 21 and 22 show modified versions of the EHD devices shown in FIGS. 1 and 2, respectively. These devices 1b and 1c differ from those shown in FIGS. 1 and 2 in that a second reservoir 50 is provided coupled by a pipe 51 to a solvent container in the form of a shroud or collar 52 surrounding the liquid outlet tube 9. The reservoir 50 contains a supply of solvent which is supplied by the pipe 51 to the shroud as a rate which substantially matches evaporation of solvent from the container 52. In this example the container 52 contains an absorbent material such as felt. It will of course be appreciated that although the liquid supply tube 9 provides a convenient place to mount the container 52, the container 52 could be mounted at any convenient place within the second chamber 5. These modified EHD devices may be used alone or as the EHD unit 103 in any of the inhalation apparatus described above to increase the solvent vapour pressure in the second chamber and can replace the bubble chamber shown in FIG. 17, enabling the air adaptation unit to be omitted.

Generally the solvent will be a solvent used in the liquid formulation being sprayed, such as ethanol, for example.

It may also be possible where removal of vapour is required to use the shroud or collar (without the reservoir 50) to contain an appropriate desiccant (for example silica gel to dry the air in the second chamber to facilitate solvent evaporation from droplets to reduce their size, also enabling omission of the air adaptation unit where drying of the ambient air is required.

In the above described examples the EHD process results in droplets. Where the liquid formulation contains a polymer then the amount of polymer may be such that comminution does not occur but rather a continuous fibre is formed which may break up into fibrils. Generally such formulations would not be used for inhalation purposes (unless the fibre breaks up into small fibrils) but may be used for topical application to wound surfaces or the interior of the mouth, for example. In these cases, the modified devices shown in FIGS. 21 and 22 may be used to control the rate at which the liquid issuing from the liquid supply tube solidifies to control the process of fibre formation rather then to prevent solidification entirely.

Where the liquid formulation contains a polymer, particularly where it contains a relatively large amount of polymer, a classical Taylor cone will generally not be produced, rather the emerging liquid will form a rather more hemi-spherical or blob-like shape at the liquid supply tube outlet. The term cone as used herein is intended to cover both the classical Taylor cone and these shapes.

Methods, devices and inhalation apparatus embodying the invention may be used to deliver biological material, water-soluble drugs or medicaments, vaccines and other delicate molecules to internal or external bodily surfaces including the lungs, trachea, throat, mouth, nasal passages, eyes and skin and wound surfaces.

APPENDIX

(A) Trypsin Assay

1 Principle $$BAEE + H_2O \xrightarrow{Trypsin} N\alpha\text{-Benzoyl-L-Arginine} + Ethanol$$

(BABE=Nα-Benzoyl-L-Arginine Ethyl Ester)

2 Conditions

Temperature=25° C., pH=7.6, wavelength=253 nm

3 Reagents 3.1 Standard Trypsin Assay (1) 67 mM sodium phosphate buffer, pH 7.6 at 25° C.

(2) 025 mM Nα-Benzoyl-L-Arginine Ethyl Ester (BAEE) in reagent (1)

(3) 1 mM hydrochloric acid (4) Immediately before use, prepare a solution containing 500 BAEE units/ml of trypsin in cold reagent (3).

3.2 Trypsin Assay Before and after Spraying (1) Blank Solution:
 (a) mix 1 ml 67 mM sodium phosphate with 4 ml PEG200,
 (b) transfer 100 µl of (5a) to 2 ml 67 mM sodium phosphate,
 (c) transfer 900 µl of (5b) to 100 µl 10 mM hydrochloric acid (1) Pre-spray solution (equivalent to 1070 BAEE units/ml trypsin):
 (a) mix 1 ml trypsin (12480 unit/ml) in 67 mM sodium phosphate with 4 ml PEG200,
 (b) transfer 100 µl of (6a) to 2 ml 67 mM sodium phosphate,
 (c) transfer 900 µl of (6b) to 100 µl 10 mM hydrochloric acid (1) Post-Spray Solution:
 (a) spray 100 µl of (6a) through a nozzle at 12 kV, with a flow rate of 1.5 µl/sec, to 2 ml 67 mM sodium phosphate
 (b) transfer 900 µl of (7a) to 100 µl 10 mM hydrochloric acid 4 Procedures 4.1 Standard Trypsin Assay Blank: 1.5 ml reagent (2)+100 µl reagent (3)

Test: 1.5 ml reagent (2)+100 µl reagent (4)

4.2 Trypsin Assay Before and after Spraying

Blank: 1.5 ml reagent (2)+100 µl reagent (5c)

Pre-spray: 1.5 ml reagent (2)+100 µl reagent (6b)

Post-spray: 1.5 ml reagent (2)+100 µl reagent (7b)

Since only microcuvette is available, the reaction mix is reduced to 1.6 ml as the final volume. Final concentrations of the reaction mix remain unchanged and are: 0.2344 mM BAEE buffer, 62.8125 mM sodium phosphate buffer and 0.0625 mM HC1.

5 Unit Definition

One BAEE unit will produce a $\Delta_{A253\,nm}$ of 0.001 per minute with BAEE as substrate at pH 7.6 at 25"C in a reaction volume of 3.2 ml.

6 Calculations

BAEE units/ml trypsin=$\Delta_{A253\,nm}/(0.001)(0.2)$ 0.001=the change in/minute per unit of trypsin at pH 7.6 at 25° C. in a 3.2 ml reaction mix 0.2=volume (in ml) of trypsin used

(B) Peroxidase Assay

1 Principle $$ABTS + H_2O_2 \xrightarrow{Peroxidase} \text{Oxidised ABTS} + 2 H_2O$$

(light green) (dark green)

(ABTS=2,2'-Azino-bis(3-Ethylbenztiazoline-6-Sulfonic Acid)

2 Conditions

Temperature=25° C., pH=5.0, wavelength=405 nm

3 Reagents 3.1 Standard Peroxidase Assay (1) 100 mM potassium phosphate buffer, pH 5.0 at 25° C. [reagent (1)]

(2) 9.1 mM ABTS substrate solution in reagent (1), Prepare fresh (3) Peroxidase diluent
 (40 mM potassium phosphate buffer with 0.25% (w/v) Bovine Serum Albumin and 0.5% (v/v) Triton X-100, pH 6.8 at 25° C.)

(4) Peroxidase solution (Immediately before use, prepare a solution containing 0.5 unit/ml of peroxidase in cold reagent (3).

(5) 0.3% (w/w) hydrogen peroxide solution 3.2 Peroxidase Assay Before and after Spraying
(6) Blank solution:
(a) add 100 μl 20% peroxidase diluent 80% PEG200 to 2 ml peroxidase diluent.
(7) Pre-spray solution:
(a) add 1 ml peroxidase (12 unit/ml) to 20% peroxidase diluent 80% PEG200.
(b) add 100 μl 7(a) to 20% peroxidase diluent 80% PEG200 (0.57 unit/ml).
(8) Post-spray solution:
(a) spray 100 μl of (7a) through a nozzle at 11.9 kV, with a flow rate of 1 μl/sec, to 2 ml peroxidase diluent.

4. Procedures 4.1 Standard Peroxidase Assay
Blank: 2.9 ml reagent 2 (ABTS)+50 μl reagent 3 (peroxidase diluent)+100 μl reagent 5 ($H_2O_2$)
Test: 2.9 ml reagent 2 (ABTS)+50 μl reagent 4 (peroxidase solution)+100 reagent 5 ($H_2O_2$)
Immediately mix by inversion and record the increase in A405 nm for 100 seconds.

4.2 Peroxidase Assay Before and after Spraying
Blank: 2.9 ml reagent (2)+50 μl reagent (6a)+100 μl reagent 5 ($H_2O_2$)
Pre-spray: 2.9 ml reagent (2)+50 μl reagent (7b)+100 μl reagent 5 ($H_2O_2$)
Post-spray: 2.9 ml reagent (2)+50 μl reagent (8a)+100 μl reagent 5 ($H_2O_2$)
Immediately mix by inversion and record the increase in A405 nm for 100 seconds.

5 Unit Definition
One unit will oxidise 1.0 μmole of ABTS per minute at pH 5.0 at 25'C 6 Final Assay Concentrations
In a 3.05 ml reaction mix, the final concentrations are:
96 mM potassium phosphate
8.7 mM ABTS
0.01% (w/w) hydrogen peroxide
0.004% (w/v) bovine serum albumin
0.008% (v/v) Triton X-100

7 Calculations units/ml peroxidase=$(\Delta_{A405\ nm})(3.05)/(36.8)(0.05)$ 3.05=Total volume (in ml) of assay 36.8=Millimolar extinct coefficient of oxidised ABTS at 405 nm 0.05=volume (in ml) of peroxidase used

The invention claimed is:

1. A method of delivering biological material in the form of a liquid aerosol, said method comprising the steps of supplying a liquid formulation comprising biological material to an outlet;
subjecting the liquid formulation issuing from the outlet to an electric field, wherein the liquid formulation is processed electrohydrodynamically in a manner sufficient to cause a cone and a jet, such that comminuted matter is formed and the biological material is not substantially denatured,
wherein the liquid formulation comprises surfactant at a concentration significantly greater than its critical micelle concentration and in an amount sufficient to allow a monolayer to be distributed over the comminuted matter; and
wherein the biological material is selected from the group consisting of DNA, DNA fragments, plasmids, RNA, proteins, peptides, hormones, lipids, enzymes and cytokines.

2. A method of delivering biological material in the form of a liquid aerosol according to claim 1, which method comprises providing a liquid formulation containing the biological material, supplying the liquid formulation to an outlet and subjecting liquid issuing from the outlet to an electric field sufficient to cause comminution of the liquid to produce droplets containing the biological material wherein the biological material is not substantially denatured.

3. A method according to claim 1, which comprises providing the liquid formulation by adding surfactant and polymer to a formulation containing the biological material before supplying the liquid formulation to the outlet.

4. A method according to claim 1, which comprises adding as the surfactant a material selected from the group consisting of didodecyldimethylammonium bromide, benzalkonium chloride, and polyethoxylated nonionic surfactants.

5. A method according to claim 1, of processing an aqueous formulation containing biological material, which method comprises adding surfactant to the liquid to provide a surfactant-concentration significantly greater than its critical micelle concentration, then supplying the surfactant-containing liquid to an outlet and subjecting the surfactant-containing liquid that issues from the outlet to an electric field sufficient to cause formation of a cone and jet.

6. A method according to claim 1, which comprises adding as the surfactant approximately 0.5% by mass of didodecyldimethylammonium bromide.

7. A method according to claim 1, which comprises adding as the surfactant 0.1% by mass of benzalkonium chloride in water.

8. A method according to claim 1, which comprises adding as the surfactant 0.8% by mass of a polyethoxylated nonionic surfactant in water.

9. A method according to claim 1, wherein the biological material is a protein material selected from the group consisting of DNA, DNA fragments, plasmids, RNA, proteins and peptides.

10. A method according to claim 1, wherein the aerosolized liquid formulation is inhaled by a patient in the form of a liquid.

11. A method according to claim 1, which comprises providing the liquid formulation by removing salts from a formulation containing biological material that does not denature in alcohol and then adding an alcohol to the formulation before supplying the liquid formulation to the outlet.

12. A method according to claim 1, which further comprises adding an acid to the liquid formulation before supplying the liquid formulation to the outlet.

13. A method according to claim 1, which comprises providing the liquid formulation by adding polymer to a formulation containing the biological material before supplying the liquid formulation to the outlet.

* * * * *